US 6,669,669 B2

(12) United States Patent
Flaherty et al.

(10) Patent No.: US 6,669,669 B2
(45) Date of Patent: Dec. 30, 2003

(54) LAMINATED PATIENT INFUSION DEVICE

(75) Inventors: J. Christopher Flaherty, Topsfield, MA (US); John T. Garibotto, Charlestown, MA (US)

(73) Assignee: Insulet Corporation, Beverly, MA (US)

( * ) Notice: Subject to any disclaimer, the term of this patent is extended or adjusted under 35 U.S.C. 154(b) by 0 days.

(21) Appl. No.: 09/977,434

(22) Filed: Oct. 12, 2001

(65) Prior Publication Data

US 2003/0073952 A1 Apr. 17, 2003

(51) Int. Cl.$^7$ ............................................... A61M 37/00
(52) U.S. Cl. .............. 604/132; 604/890.1; 128/DIG. 12
(58) Field of Search ................ 604/151, 890, 604/891.1, 30–34, 65, 67, 118, 122, 123, 153, 131–133, 140–143, 187, 110, 236, 237, 288.01–288.03; 128/DIG. 12; 222/56, 61, 189.06, 212, 213, 550

(56) References Cited

U.S. PATENT DOCUMENTS

| 306,691 A | 3/1884 | Arai |
| 303,013 A | 8/1884 | Konopka |
| 315,727 A | 3/1885 | Arai et al. |
| 311,735 A | 10/1885 | Aran et al. |
| 405,524 A | 2/1889 | Falk et al. |
| 3,631,847 A | 1/1972 | Hobbs |
| 3,812,843 A | 5/1974 | Wootten et al. |
| 4,067,000 A | 1/1978 | Carlson |
| 4,108,177 A | 8/1978 | Pistor |
| 4,151,845 A | 5/1979 | Clemens |
| 4,211,998 A | 7/1980 | Junginger et al. |
| 4,231,019 A | 10/1980 | Junginger et al. |
| 4,268,150 A | 5/1981 | Chen |
| 4,364,385 A | 12/1982 | Lossef |
| 4,373,527 A | 2/1983 | Fischell |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,514,732 A | 4/1985 | Hayes, Jr. |
| 4,529,401 A | 7/1985 | Leslie et al. |
| 4,551,134 A | 11/1985 | Slavik et al. |

(List continued on next page.)

FOREIGN PATENT DOCUMENTS

| DE | 4200595 | 7/1993 |
| DE | 19920896 | 9/2000 |
| EP | 0342947 | 5/1989 |

(List continued on next page.)

OTHER PUBLICATIONS

US 5,954,699, 9/1999, Jost et al. (withdrawn)
Copy of PCT International Search Report dated Mar. 3, 2003.
Copy of PCT International Search Report dated Mar. 4, 2002; 5pp.

Primary Examiner—Manuel Mendez
Assistant Examiner—Cris L. Rodriguez
(74) Attorney, Agent, or Firm—McDermott, Will & Emery

(57) ABSTRACT

A device for delivering fluid to a patient including an exit port assembly adapted to connect to a transcutaneous patient access tool, and a dispenser including at least two laminated layers of material defining a passageway connected to the exit port assembly, and an expandable accumulator in fluid communication with the passageway for controlling fluid flow from a reservoir to the exit port assembly. The laminated construction provides many benefits including simplifying the design and manufacturing of the device, in order to further reduce the size, complexity and costs of the device so that the device lends itself to being small and disposable in nature.

16 Claims, 15 Drawing Sheets

U.S. PATENT DOCUMENTS

| | | | |
|---|---|---|---|
| 4,559,033 A | 12/1985 | Stephen et al. | |
| 4,559,037 A | 12/1985 | Franetzki et al. | |
| 4,560,979 A | 12/1985 | Rosskopk | |
| 4,562,751 A | 1/1986 | Nason et al. | |
| 4,585,439 A | 4/1986 | Michel | |
| 4,601,707 A | 7/1986 | Albisser et al. | |
| 4,624,661 A | 11/1986 | Arimond | |
| 4,634,427 A | 1/1987 | Hannula et al. | |
| 4,678,408 A | 7/1987 | Nason et al. | |
| 4,684,368 A | 8/1987 | Kenyon | |
| 4,685,903 A | 8/1987 | Cable et al. | |
| 4,734,092 A | 3/1988 | Millerd | |
| 4,755,173 A | 7/1988 | Konopka et al. | |
| 4,781,688 A | 11/1988 | Thoma et al. | |
| 4,781,693 A | 11/1988 | Martinez et al. | |
| 4,801,957 A | 1/1989 | Vandemoere | |
| 4,808,161 A | 2/1989 | Kamen | |
| 4,836,752 A | 6/1989 | Burkett | |
| 4,855,746 A | 8/1989 | Stacy | |
| 4,882,600 A | 11/1989 | Van de Moere | |
| 4,886,499 A | 12/1989 | Cirelli et al. | |
| 4,898,579 A | 2/1990 | Groshong et al. | |
| 4,969,874 A | 11/1990 | Michel et al. | |
| 4,973,998 A | 11/1990 | Gates | |
| 5,007,458 A | 4/1991 | Marcus et al. | |
| 5,045,871 A | 9/1991 | Reinholdson | |
| 5,062,841 A | 11/1991 | Siegel | |
| 5,109,850 A | 5/1992 | Blanco et al. | |
| 5,176,662 A | 1/1993 | Bartholomew et al. | |
| 5,178,609 A | 1/1993 | Ishikawa | |
| 5,205,819 A | 4/1993 | Ross et al. | |
| 5,213,483 A | 5/1993 | Flaherty et al. | |
| 5,232,439 A | 8/1993 | Campbell et al. | |
| 5,239,326 A | 8/1993 | Takai | |
| 5,242,406 A | 9/1993 | Gross et al. | |
| 5,244,463 A | 9/1993 | Cordner, Jr. et al. | |
| 5,254,096 A | 10/1993 | Rondelet et al. | |
| 5,257,980 A | 11/1993 | Van Antwerp et al. | |
| 5,281,202 A | 1/1994 | Weber et al. | |
| 5,312,337 A | 5/1994 | Flaherty et al. | |
| 5,318,540 A | 6/1994 | Athayde et al. | |
| 5,342,313 A | 8/1994 | Campbell et al. | |
| 5,364,342 A | 11/1994 | Beuchat et al. | |
| 5,411,480 A * | 5/1995 | Kriesel | 604/133 |
| 5,433,710 A | 7/1995 | Van Antwerp et al. | |
| 5,452,033 A | 9/1995 | Balling et al. | |
| 5,492,534 A | 2/1996 | Athayde et al. | |
| 5,505,709 A | 4/1996 | Funderburk et al. | |
| 5,507,288 A | 4/1996 | Bocker et al. | 128/633 |
| 5,514,096 A | 5/1996 | Hiejima | |
| 5,533,389 A | 7/1996 | Kamen et al. | |
| 5,545,152 A | 8/1996 | Funderburk et al. | |
| 5,575,770 A | 11/1996 | Melsky et al. | |
| 5,576,781 A | 11/1996 | Deleeuw | |
| 5,582,593 A | 12/1996 | Hultman | |
| 5,584,813 A | 12/1996 | Livingston et al. | |
| 5,630,710 A | 5/1997 | Tune et al. | |
| 5,637,095 A | 6/1997 | Nason et al. | |
| 5,643,213 A | 7/1997 | McPhee | |
| 5,647,853 A | 7/1997 | Feldmann et al. | |
| 5,660,728 A | 8/1997 | Saaski et al. | |
| 5,665,065 A | 9/1997 | Colman et al. | |
| 5,665,070 A | 9/1997 | McPhee | |
| 5,693,018 A * | 12/1997 | Kriesel et al. | 604/132 |
| 5,695,490 A | 12/1997 | Flaherty et al. | |
| 5,702,363 A | 12/1997 | Flaherty | |
| 5,704,520 A | 1/1998 | Gross | |
| 5,716,343 A * | 2/1998 | Kriesel et al. | 604/132 |
| 5,726,404 A | 3/1998 | Brody | |
| 5,726,751 A | 3/1998 | Altendorf et al. | |
| 5,741,228 A | 4/1998 | Lambrecht et al. | |
| 5,747,350 A | 5/1998 | Sattler | |
| 5,748,827 A | 5/1998 | Holl et al. | |
| 5,755,682 A | 5/1998 | Knudson et al. | |
| 5,776,103 A | 7/1998 | Kriesel et al. | |
| 5,779,676 A | 7/1998 | Kriesel et al. | |
| 5,785,681 A | 7/1998 | Indravudh | |
| 5,785,688 A | 7/1998 | Joshi et al. | |
| 5,797,881 A | 8/1998 | Gadot | |
| 5,800,397 A | 9/1998 | Wilson | |
| 5,800,405 A | 9/1998 | McPhee | |
| 5,810,015 A | 9/1998 | Flaherty | |
| 5,814,020 A | 9/1998 | Gross | |
| 5,839,467 A | 11/1998 | Saaski et al. | |
| 5,840,063 A | 11/1998 | Flaherty | |
| 5,845,218 A | 12/1998 | Altschul | |
| 5,848,991 A | 12/1998 | Gross et al. | |
| 5,851,197 A | 12/1998 | Marano et al. | |
| 5,858,005 A | 1/1999 | Kriesel | |
| 5,875,393 A | 2/1999 | Altschul et al. | |
| 5,886,647 A | 3/1999 | Badger et al. | |
| 5,891,097 A | 4/1999 | Saito et al. | |
| 5,897,530 A | 4/1999 | Jackson | |
| 5,906,597 A | 5/1999 | McPhee | |
| 5,911,716 A | 6/1999 | Rake et al. | |
| 5,919,167 A | 7/1999 | Mulhauser et al. | |
| 5,931,814 A | 8/1999 | Alex et al. | |
| 5,935,099 A | 8/1999 | Peterson et al. | |
| 5,954,058 A | 9/1999 | Flaherty | |
| 5,957,890 A | 9/1999 | Mann et al. | |
| 5,961,492 A | 10/1999 | Kriesel et al. | |
| 5,965,848 A | 10/1999 | Altschul et al. | |
| 5,983,094 A | 11/1999 | Altschul et al. | |
| 5,993,423 A | 11/1999 | Choi | |
| 5,997,501 A | 12/1999 | Gross et al. | |
| 6,019,747 A | 2/2000 | McPhee | |
| 6,061,580 A | 5/2000 | Altschul et al. | |
| 6,071,292 A | 6/2000 | Makower et al. | |
| 6,144,847 A | 11/2000 | Altschul et al. | |
| 6,152,898 A | 11/2000 | Olsen | |
| 6,174,300 B1 | 1/2001 | Kriesel et al. | |
| 6,190,359 B1 | 2/2001 | Heruth | |
| 6,200,293 B1 * | 3/2001 | Kriesel et al. | 604/132 |
| 6,375,638 B2 | 4/2002 | Nason et al. | |
| 6,485,463 B1 * | 11/2002 | Yeh | 604/132 |
| 6,488,652 B1 * | 12/2002 | Weijand et al. | 604/93.01 |
| 6,527,744 B1 | 3/2003 | Kriesel et al. | |

FOREIGN PATENT DOCUMENTS

| | | |
|---|---|---|
| EP | 0763369 | 3/1997 |
| EP | 0867196 | 3/1998 |
| EP | 0937475 | 8/1999 |
| WO | WO 81/01658 | 6/1981 |
| WO | WO86/06796 | 11/1986 |
| WO | WO98/00193 | 1/1998 |
| WO | WO98/01071 | 1/1998 |
| WO | WO99/10040 | 3/1999 |
| WO | WO00/19887 | 9/1999 |
| WO | WO99/62576 | 9/1999 |
| WO | WO99/56803 | 11/1999 |
| WO | WO0010628 | 3/2000 |
| WO | WO00/29047 | 5/2000 |
| WO | WO00/29049 | 5/2000 |
| WO | WO00/74752 | 5/2000 |
| WO | WO00/30705 | 6/2000 |
| WO | WO00/78210 | 6/2000 |

| | | | | | |
|---|---|---|---|---|---|
| WO | WO00/48112 | 8/2000 | WO | WO01/76684 | 10/2001 |
| WO | WO00/61215 | 10/2000 | WO | WO 02/20073 | 3/2002 |
| WO | WO01/52727 | 1/2001 | WO | WO02/26282 | 4/2002 |
| WO | WO001/5663 | 8/2001 | | | |

* cited by examiner

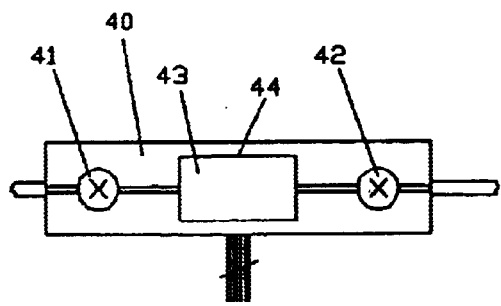
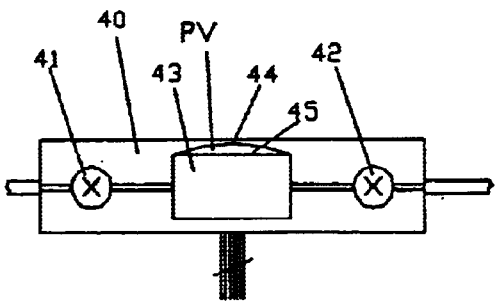
Fig. 3a  Fig. 3b
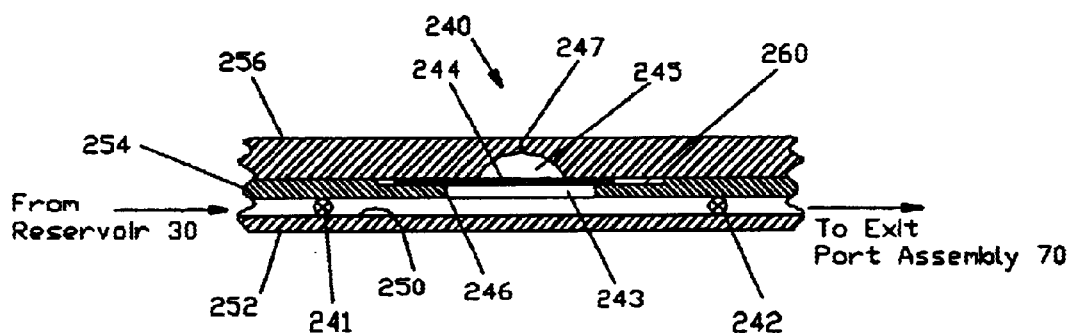
Fig. 4a
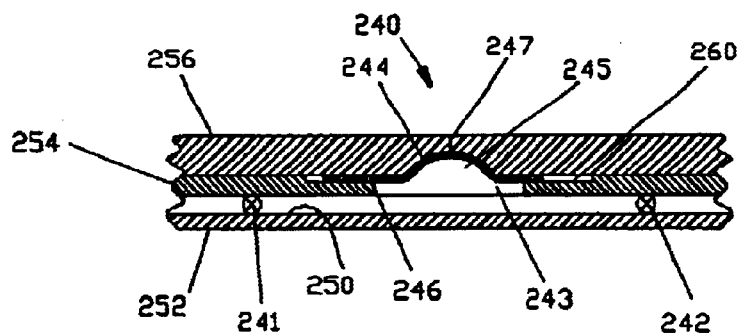
Fig. 4b

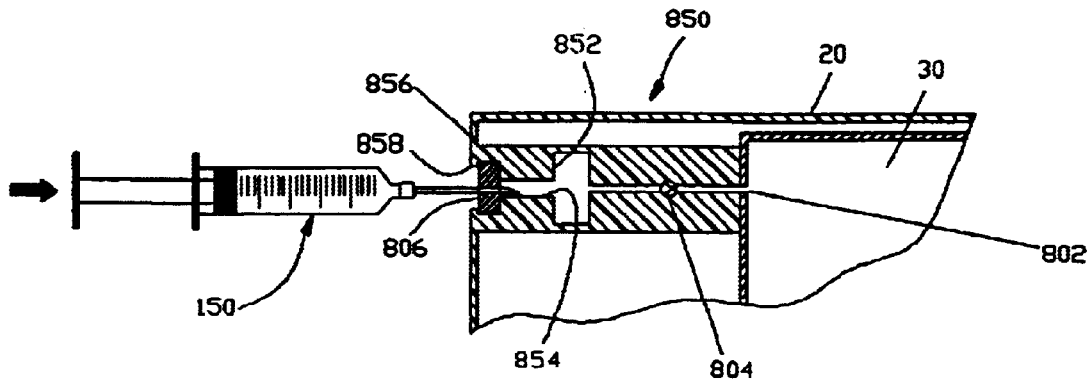
Fig. 30a
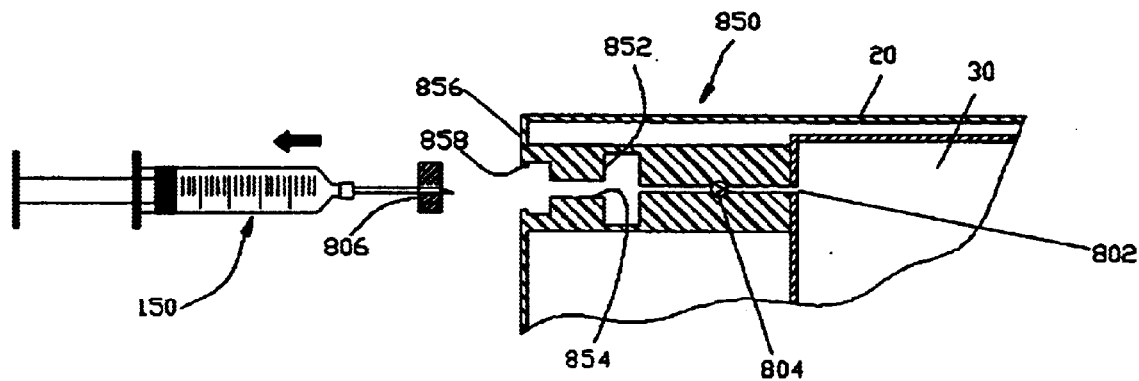
Fig. 30b
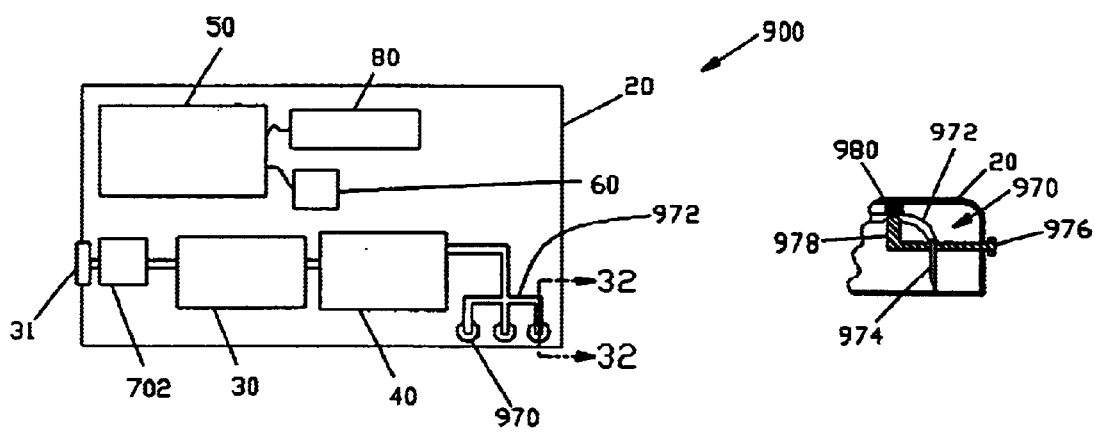
Fig. 31
Fig. 32

LAMINATED PATIENT INFUSION DEVICE

CROSS-REFERENCE TO RELATED APPLICATIONS

The present application is related to U.S. patent application Ser. No. 09/943,992, filed on Aug. 31, 2001, which is assigned to the assignee of the present application and incorporated herein by reference.

FIELD OF THE INVENTION

The present invention relates generally to medical devices, systems and methods, and more particularly to small, low cost, portable infusion devices and methods that are useable to achieve precise, sophisticated, and programmable flow patterns for the delivery of therapeutic liquids to a mammalian patient.

BACKGROUND OF THE INVENTION

Today, there are numerous diseases and other physical ailments that are treated by various medicines including pharmaceuticals, nutritional formulas, biologically derived or active agents, hormonal and gene based material and other substances in both solid or liquid form. In the delivery of these medicines, it is often desirable to bypass the digestive system of a mammalian patient to avoid degradation of the active ingredients caused by the catalytic enzymes in the digestive tract and liver. Delivery of a medicine other than by way of the intestines is known as parenteral delivery. Parenteral delivery of various drugs in liquid form is often desired to enhance the effect of the substance being delivered, insuring that the unaltered medicine reaches its intended site at a significant concentration. Also, undesired side effects associated with other routes of delivery, such as systemic toxicity, can potentially be avoided.

Often, a medicine may only be available in a liquid form, or the liquid version may have desirable characteristics that cannot be achieved with solid or pill form. Delivery of liquid medicines may best be accomplished by infusing directly into the cardiovascular system via veins or arteries, into the subcutaneous tissue or directly into organs, tumors, cavities, bones or other site specific locations within the body.

Parenteral delivery of liquid medicines into the body is often accomplished by administering bolus injections using a needle and reservoir, or continuously by gravity driven dispensers or transdermal patch technologies. Bolus injections often imperfectly match the clinical needs of the patient, and usually require larger individual doses than are desired at the specific time they are given. Continuous delivery of medicine through gravity feed systems compromise the patient's mobility and lifestyle, and limit the therapy to simplistic flow rates and profiles. Transdermal patches have special requirements of the medicine being delivered, particularly as it relates to the molecular structure, and similar to gravity feed systems, the control of the drug administration is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. An example of a use of an ambulatory infusion pump is for the delivery of insulin for the treatment of diabetes mellitus. These pumps can deliver insulin on a continuous basal basis as well as a bolus basis as is disclosed in U.S. Pat. No. 4,498,843 to Schneider et al.

The ambulatory pumps often work with a reservoir to contain the liquid medicine, such as a cartridge or reservoir, and use electromechanical pumping or metering technology to deliver the medication to the patient via tubing from the infusion device to a needle that is inserted transcutaneously, or through the skin of the patient. The devices allow control and programming via electromechanical buttons or switches located on the housing of the device, and accessed by the patient or clinician. The devices include visual feedback via text or graphic screens, such as liquid crystal displays known as LCD's, and may include alert or warning lights and audio or vibration signals and alarms. The device can be worn in a harness or pocket or strapped to the body of the patient.

Currently available ambulatory infusion devices are expensive, difficult to program and prepare for infusion, and tend to be bulky, heavy and very fragile. Filling these devices can be difficult and require the patient to carry both the intended medication as well as filling accessories. The devices require specialized care, maintenance, and cleaning to assure proper functionality and safety for their intended long term use. Due to the high cost of existing devices, healthcare providers limit the patient populations approved to use the devices and therapies for which the devices can be used.

Clearly, therefore, there was a need for a programmable and adjustable infusion system that is precise and reliable and can offer clinicians and patients a small, low cost, light weight, simple to use alternative for parenteral delivery of liquid medicines.

In response, the applicant of the present application provided a small, low cost, light weight, easy to use device for delivering liquid medicines to a patient. The device, which is described in detail in co-pending U.S. application Ser. No. 09/943,992, filed on Aug. 31, 2001, includes an exit port, a dispenser for causing fluid from a reservoir to flow to the exit port, a local processor programmed to cause a flow of fluid to the exit port based on flow instructions from a separate, remote control device, and a wireless receiver connected to the local processor for receiving the flow instructions. To reduce the size, complexity and costs of the device, the device is provided with a housing that is free of user input components, such as a keypad, for providing flow instructions to the local processor.

What is still desired are new and improved devices for delivering fluid to a patient. Preferably, the fluid delivery devices will be simple in design, and inexpensive and easy to manufacture, in order to further reduce the size, complexity and costs of the devices, such that the devices lend themselves to being small and disposable in nature.

SUMMARY OF THE INVENTION

In response, the present invention provides a device for delivering fluid to a patient, including an exit port assembly adapted to connect to a transcutaneous patient access tool, and a dispenser including at least two laminated layers of material defining a passageway connected to the exit port assembly, and an expandable accumulator in fluid communication with the passageway for controlling fluid flow from a reservoir to the exit port assembly. The laminated construction provides many benefits including, but not limited to, simplifying the design and manufacturing of the device, and further reducing the size, complexity and costs of the device. The device of the present invention, therefore, lends itself to being small and disposable in nature.

According to one aspect of the present invention, at least one layer of the dispenser comprises a resilient diaphragm. According to another aspect, the at least two laminated layers of the dispenser further include a first layer and a second layer received against the first layer. The second and the first layers define the passageway connected to the exit port assembly, and the second layer includes an opening in fluid communication with the passageway. The resilient diaphragm is received on the second layer covering the opening, and a third layer is received over the diaphragm on the second layer. The third layer has an pulse chamber over the diaphragm and in alignment with the opening of the second layer, and a port in fluid communication with the pulse chamber.

According to another aspect, one of the second and the third layers defines a recess receiving the diaphragm, and wherein the recess has a depth about equal to a thickness of the diaphragm such that the diaphragm is secured in a substantially fluid-tight manner between the second and the third layers. Preferably, a length and a width of the recess are greater than a length and a width of the diaphragm in order to decrease required manufacturing tolerances of the dispenser.

According to an additional embodiment of the present invention, the at least two laminated layers include a first layer, and a second layer received against the first layer. The second and the first layers define the passageway connected to the exit port assembly. The second layer includes a surface facing away from the first layer and having a recess, and an opening providing fluid communication between the recess and the passageway defined by the first and the second layers. The resilient diaphragm is received on the second layer covering the recess to form the expandable accumulator.

According to one aspect, the device includes an actuator for pushing the diaphragm into the recess to reduce the volume of the accumulator. According to another aspect, the actuator comprises a rotatable cam.

According to another embodiment, a third layer is received against the diaphragm and has a bore aligned with the recess of the second layer, and the actuator comprises a piston slidingly received in the bore. According to one aspect, a magnetic coil is received in the third layer coaxial with the piston for biasing the piston against the diaphragm upon being electrified. According to another aspect, the dispenser includes multiple accumulators arranged sequentially with respect to the passageway, and magnetic coils and pistons associated with each accumulator.

According to another embodiment, a third layer is received against the diaphragm and has a bore aligned with the recess of the second layer, and a fourth layer is received against the third layer and has a bore aligned with the bore of the third layer, and a gas generator is received in the bore of the fourth layer for pressurizing the bore and biasing the piston against the diaphragm upon being actuated. According to one aspect, the dispenser includes multiple accumulators arranged sequentially with respect to the passageway, and gas generators and pistons associated with each accumulator.

According to a further embodiment, the dispenser includes a first layer having a surface defining a groove, with the diaphragm positioned against the surface of the first layer such that the diaphragm and the groove define the passageway connected to the exit port assembly. A second layer is received against the diaphragm and includes a recess separated from the passageway by the diaphragm, and the portion of the passageway opposite the recess comprises the expandable accumulator. An actuator is received in the recess of the second layer for pushing the diaphragm towards the first layer upon being actuated to reduce the volume of the accumulator. According to one aspect, the actuator comprises a piece of piezoelectric material arranged to push the diaphragm upon contracting. According to another aspect, the actuator comprises multiple pieces of piezoelectric material arranged sequentially with respect to the passageway within the recess.

Another embodiment includes a first layer received against a second layer, with the layers defining the passageway connected to the exit port assembly, and the second layer including a recess facing the first layer. The dispenser further includes a piston slidingly received in the recess of the second layer, such that the piston and the recess define the expandable accumulator. According to one aspect, a spring biases the piston towards the first layer. According to another aspect, a magnetic coil is received in the second layer coaxial with the piston for biasing the piston towards the first layer upon being electrified.

These aspects of the invention together with additional features and advantages thereof may best be understood by reference to the following detailed descriptions and examples taken in connection with the accompanying illustrated drawings.

BRIEF DESCRIPTION OF THE DRAWINGS

FIGS. 3a and 3b are sectional side views of a dispenser of the fluid delivery device of FIG. 1, illustrating operation of the dispenser;

FIGS. 4a and 4b are sectional views of another dispenser constructed in accordance with the present invention, illustrating operation of the dispenser;

FIGS. 30a and 30b are sectional views of another embodiment of a fill port constructed in accordance with the present disclosure, and illustrating operation of the fill port;

FIG. 31 is a top sectional view of another device constructed in accordance with the present invention; and FIG. 32 is a side elevation view, partially cut away, of the device of FIG. 31.

Like reference characters designate identical or corresponding components and units throughout the several views.

DETAILED DESCRIPTION OF THE PREFERRED EMBODIMENTS

Figure 1:
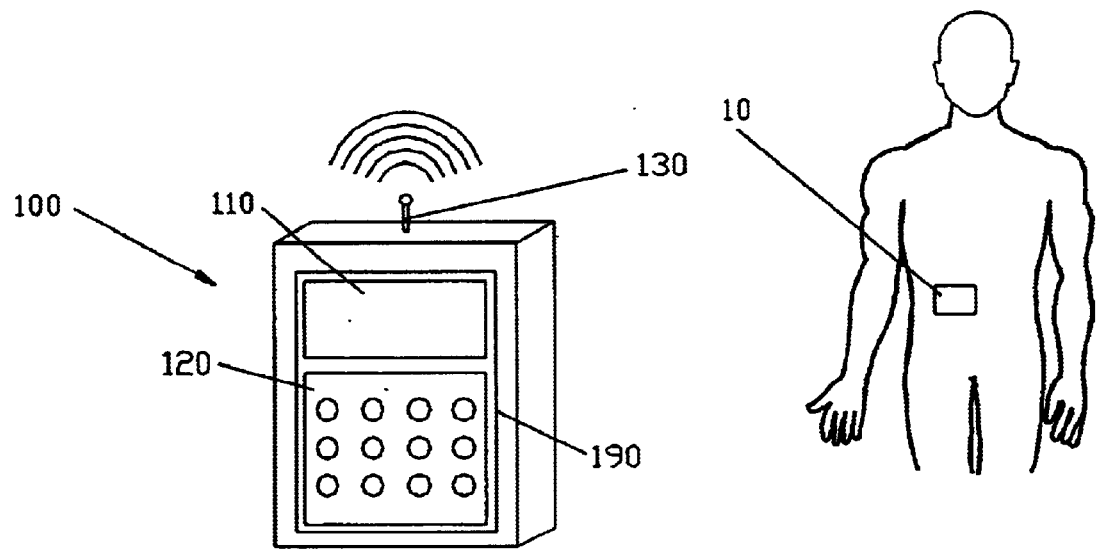
FIG. 1 is a perspective view of a first exemplary embodiment of a fluid delivery device in accordance with this invention shown secured on a patient, and a remote control device for use with the fluid delivery device (the remote control device being enlarged with respect to the patient and the fluid delivery device for purposes of illustration)
Figure 2:
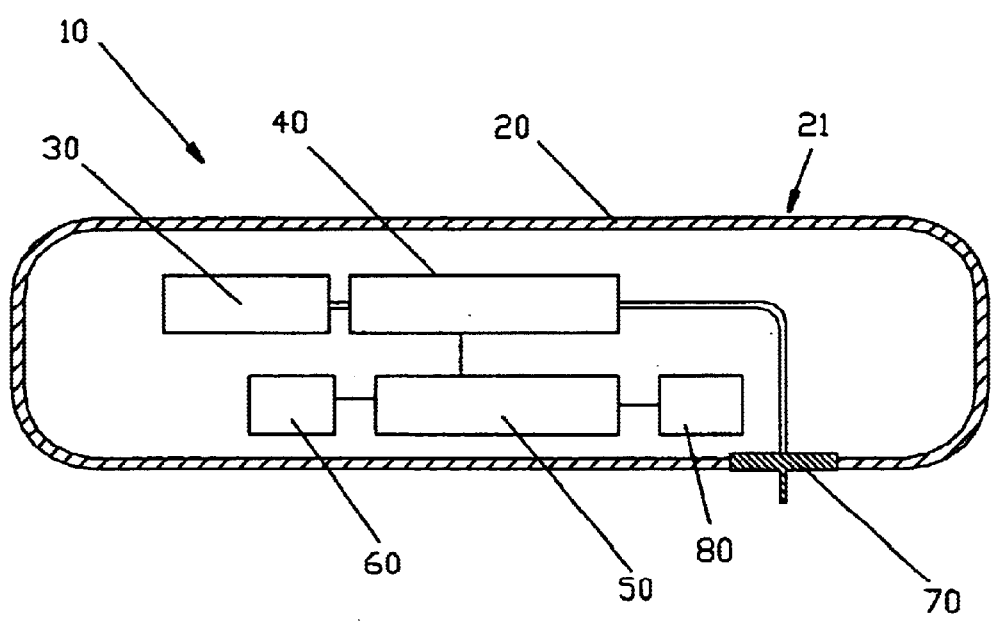
FIG. 2 is a sectional side view of the fluid delivery device of FIG. 1.

Referring first to FIGS. 1 and 2, there is illustrated a fluid delivery device 10 constructed in accordance with the present invention. The types of liquids that can be delivered by the fluid delivery device of the present invention include, but are not limited to, insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The types of medical conditions that the fluid delivery device of the present invention might be used to treat include, but are not limited to, diabetes, cardiovascular disease, pain, chronic pain, cancer, AIDS, neurological diseases, Alzheimer's Disease, ALS, Hepatitis, Parkinson's Disease or spasticity.

Referring to FIG. 2, the device 10 generally includes an exit port assembly 70 adapted to connect to a transcutaneous patient access tool such as a needle, a dispenser 40 for causing fluid from a reservoir 30 to flow to the exit port assembly 70, and a processor or electronic microcontroller (hereinafter referred to as the "local" processor) 50 connected to the dispenser 40.

The local processor 50 is programmed to cause a flow of fluid to the exit port assembly 70 based on flow instructions from a separate, remote control device 100, an example of which is shown in FIG. 1. Referring also to FIG. 2, the fluid delivery device 10 further includes a wireless receiver 60 connected to the local processor 50 for receiving the flow instructions from the separate, remote control device 100 and delivering the flow instructions to the local processor. The device 10 also includes a housing 20 containing the exit port assembly 70, the reservoir 30, the dispenser 40, the local processor 50, and the wireless receiver 60.

As shown, the housing 20 is free of user input components for providing flow instructions to the local processor 50, such as electromechanical switches or buttons on an outer surface 21 of the housing, or interfaces otherwise accessible to a user to adjust the programmed flow rate through the local processor 50. The lack of user input components allows the size, complexity and costs of the device 10 to be substantially reduced so that the device 10 lends itself to being small and disposable in nature.

In order to program, adjust the programming of, or otherwise communicate user inputs to the local processor 50, the fluid delivery device 10 includes the wireless communication element, or receiver 60 for receiving the user inputs from the separate, remote control device 100 of FIG. 1. Signals can be sent via a communication element (not shown) of the remote control device 100, which can include or be connected to an antenna 130, shown in FIG. 1 as being external to the device 100.

The remote control device 100 has user input components, including an array of electromechanical switches, such as the membrane keypad 120 shown. The control device 100 also includes user output components, including a visual display, such as a liquid crystal display (LCD) 110. Alternatively, the control device can be provided with a touch screen for both user input and output. Although not shown in FIG. 1, the remote control device 100 has its own processor (hereinafter referred to as the "remote" processor) connected to the membrane keypad 120 and the LCD 110. The remote processor receives the user inputs from the membrane keypad 120 and provides "flow" instructions for transmission to the fluid delivery device 10, and provides information to the LCD 110. Since the remote control device 100 also includes a visual display 110, the fluid delivery device 10 can be void of an information screen, further reducing the size, complexity and costs of the device 10.

The communication element 60 of the device 10 preferably receives electronic communication from the remote control device 100 using radio frequency or other wireless communication standards and protocols. In a preferred embodiment, the communication element 60 is a two-way communication element, including a receiver and a transmitter, for allowing the fluid delivery device 10 to send information back to the remote control device 100. In such an embodiment, the remote control device 100 also includes an integral communication element 60 comprising a receiver and a transmitter, for allowing the remote control device 100 to receive the information sent by the fluid delivery device 10.

The local processor 50 of the device 10 contains all the computer programs and electronic circuitry needed to allow a user to program the desired flow patterns and adjust the program as necessary. Such circuitry can include one or more microprocessors, digital and analog integrated circuits, resistors, capacitors, transistors and other semiconductors and other electronic components known to those skilled in the art. The local processor 50 also includes programming, electronic circuitry and memory to properly activate the dispenser 40 at the needed time intervals.

In the exemplary embodiment of FIG. 2, the device 10 includes a power supply 80, such as a battery or capacitor, for supplying power to the local processor 50. The power supply 80 is preferably integrated into the fluid delivery device 10, but can be provided as replaceable, e.g., a replaceable battery.

Although not shown, the device can include sensors or transducers such as a reservoir volume transducer or a reservoir pressure transducer, for transmitting information to the local processor 50 to indicate how and when to activate the dispenser 40, or to indicate other parameters determining flow, pump flowpath prime condition, blockage in flowpath, contact sensors, rotary motion or other motion indicators, as well as conditions such as the reservoir 30 being empty or leaking, or the dispensing of too much or too little fluid from the reservoir, etc.

The volume of the reservoir 30 is chosen to best suit the therapeutic application of the fluid delivery device 10 impacted by such factors as available concentrations of medicinal fluids to be delivered, acceptable times between refills or disposal of the fluid delivery device 10, size constraints and other factors. The reservoir 30 may be prefilled by the device manufacturer or a cooperating drug manufacturer, or may include external filling means, such as a fill port having needle insertion septum or a Luer connector, for example. In addition, the device 10 can be provided with a removable reservoir.

The exit port assembly 70 can include elements to penetrate the skin of the patient, or can be adapted to connect to a standard infusion device that includes transcutaneous delivery means. A needle connection tubing terminating in a skin penetrating cannula (not shown) can be provided as an integral part of the exit port assembly 70, for example, with the skin penetrating cannula comprising a rigid member, such as a needle. Alternatively, the exit port assembly 70 can be provided with a Luer connector for connecting to a standard infusion device including a skin penetrating cannula, such as a rigid needle. In the preferred embodiment, the exit port assembly 70 includes injection means, such as a spring driven mechanism, to assist in penetrating the skin with the skin penetrating cannula. If the cannula is a flexible tube, a rigid penetrator within the lumen of the tube is driven through the skin by the injection means, and withdrawn leaving the soft cannula in place, such as in the subcutaneous tissue of the patient or other internal site. The injection means may be integral to the device 10, or removable soon after transcutaneous penetration. In any event, the exit port assembly 70 can also be provided with a removable plug (not shown) for preventing leakage during storage and shipment if pre-filled, and during priming if filled by user, and prior to use.

The device 10 can also be provided with an adhesive layer on the outer surface of the housing 20 for securing the device 10 directly to the skin of a patient, as shown in FIG. 1. Although not shown, the adhesive layer is preferably provided in a continuous ring encircling the exit port assembly 70 in order to provide a protective seal around the penetrated skin. The housing 20 can be made from flexible material, or can be provided with flexible hinged sections that allow the fluid delivery device 10 to flex during patient movement to prevent detachment and aid in patient comfort.

The dispenser 40 is connected in fluid communication with the reservoir 30, as shown in FIG. 2. When the device 10 is provided with a pressurized reservoir 30 (i.e., fluid maintained within the reservoir at a pressure above atmospheric), the dispenser 40 can include an inlet valve 41 connected to the reservoir, an outlet valve 42 connected to the exit port assembly 70, and an accumulator 43 connected between the inlet valve and the outlet valve, as shown in the exemplary embodiment of FIGS. 3a and 3b. Since the fluid in the reservoir 30 is maintained at a pressure above atmospheric pressure, opening of the inlet valve 41 allows the accumulator 43 to fill to the reservoir pressure, after which the inlet valve is 41 is closed. At the proper time, as determined by the local processor 50 programming and instructions received from the remote control device 100, the outlet valve 42 can be opened to dispense fluid to the exit port assembly 70, which is at the pressure of the patient, or atmospheric pressure. The accumulator 43 will then be at atmospheric pressure, and the outlet valve 42 can be closed, ready for another repeat cycle.

The dispenser 40 of the exemplary embodiment of FIGS. 3a and 3b does not create a driving or pumping force on the fluid passing therethrough, but rather acts as a metering device, allowing pulses of fluid to pass from the pressurized reservoir 30, through the dispenser 40, to the exit port assembly 70 at atmospheric pressure. The inlet valve 41 and the outlet valve 42 of the dispenser 40 are controlled by the local processor 50, which includes electronic programming, controls and circuitry to allow sophisticated fluid delivery programming and control of the dispenser 40.

FIG. 3a shows the dispenser 40 with the accumulator 43 at atmospheric pressure. An accumulator membrane 44 is shown in a non-distended state, caused by atmospheric pressure only. Inlet valve 41 is closed, and outlet valve 42 may be open or closed, but must have been opened since the last time inlet valve 41 was opened. FIG. 3b shows the condition where outlet valve 42 is closed, and inlet valve 41 has been opened. Because of the elevated pressure of the fluid from the reservoir 30, the accumulator membrane 44 is distended, thus increasing the volume of accumulator 43 by an accumulator volume 45. After the inlet valve 41 is closed, the outlet valve 42 can be opened, to dispense the accumulator volume 45 and allow the accumulator membrane 44 to retract to the position shown in FIG. 3a.

The inlet valve 41 and the outlet valve 42 of the dispenser 40 and the local processor 50 are designed to prevent both valves from being opened at the same time, precluding the reservoir 30 to ever flow directly to the exit port assembly

70. The prevention of both valves opening at the same time is critical and can be accomplished via mechanical means, electrical means, or both. The prevention can be accomplished in the dispenser 40 design, the local processor 50 design, or both.

The dispenser 40 shown in FIGS. 3a and 3b dispenses finite pulses of fluid volume, called pulse volume (PV), with each activation. The PV is determined by the properties, materials and construction of the accumulator 43 and the accumulator membrane 44. PV's delivered by infusion devices are typically chosen to be small relative to what would be considered a clinically significant volume. For insulin applications at a concentration of 100 units per ml, a PV of less than 2 microliter, and typically 0.5 microliter, is appropriate. If the fluid delivery device 10 is programmed via the remote control device 100 to deliver 2 units an hour, the dispenser will deliver 40 pulses an hour, or a pulse every 1.5 minutes. Such pulsitile flow is considered continuous if the PV is small enough. Other drugs or concentrations may permit a much larger PV. Various flow rates are achieved by adjusting the time between pulses. To give a fixed volume or bolus, multiple pulses are given in rapid succession until the bolus volume is reached.

The PV may not always be constant enough to be within the accuracy requirements of the fluid delivery device 10. One factor impacting the PV is the pressure of the reservoir 30. The fluid delivery device 10 may include means for monitoring reservoir 30 pressure and adjust the timing between pulses to achieve the desire flow pattern. An example of such compensation would be to decrease time between pulses as the reservoir 30 pressure decreases to maintain the programmed flow rate. An alternative to monitoring reservoir 30 pressure is monitoring the volume of the reservoir 30. Each time a pulse or series of pulses are delivered, a measurement of reservoir 30 volume can indicate whether a proper amount of fluid has been delivered, both for individual pulses and cumulative pulses. The system could also be designed to compensate fluid flow as errors are detected.

Referring now to FIGS. 4a and 4b, the present invention provides an improved dispenser 240 for use with the fluid delivery device 10 of FIGS. 1 and 2. Operation of the dispenser 240 of FIGS. 4a and 4b is similar to operation of the dispenser 40 of FIGS. 3a and 3b. In addition, some elements of the dispenser 240 of FIGS. 4a and 4b are similar to the dispenser 40 of FIGS. 3a and 3b such that similar elements have the same reference numeral preceded by a "2".

The dispenser 240 of FIGS. 4a and 4b, however, includes at least two laminated layers 252, 254 of material defining a passageway 250 for connection to the exit port assembly 70, and an expandable accumulator 243 in fluid communication with the passageway 250 for controlling fluid flow from the reservoir 30 to the exit port assembly 70. The laminated construction provides many benefits including, but not limited to, simplifying the design and manufacturing of the dispenser 240, and further reducing the size, complexity and costs of the dispenser 240. The dispenser 240 of the present invention, therefore, lends itself to being small and disposable in nature.

In the embodiment of FIGS. 4a and 4b, the layers of the dispenser 240 include a first layer 252 and a second layer 254 received against the first layer. At least one of the second and the first layers 252, 254 includes a surface groove between the layers which defines the passageway 250 connected to the exit port assembly 70. The second layer 254 includes an opening 246 in fluid communication with the passageway 250. The layers 252, 254 also include a resilient diaphragm 244 received on the second layer 254 covering the opening, and a third layer 256 received over the diaphragm 244 on the second layer 254. The third layer 256 has a pulse chamber 245 over the diaphragm 244 and in alignment with the opening 246 of the second layer 254, and a relief port 247 in fluid communication with the pulse chamber 245.

FIG. 4a shows the dispenser 240 with the accumulator 243 at atmospheric pressure with the resilient diaphragm 244 in a non-distended state. Inlet valve 241 is closed, and outlet valve 242 may be open or closed, but must have been opened since the last time the inlet valve 241 was opened. FIG. 4b shows the condition wherein the outlet valve 242 is closed, and the inlet valve 241 has been opened. Because of the elevated pressure of the fluid from the reservoir 30, the fluid expands the resilient diaphragm 244 into the pulse chamber 245 (with the relief port 247 allowing evacuation of the pulse chamber 245), thus increasing the volume of the accumulator 243 by about a volume of the pulse chamber 245. After the inlet valve 241 is closed, the outlet valve 242 can be opened, to dispense the accumulator volume 245 and allow the resilient diaphragm 244 to return to the position shown in FIG. 4a.

The laminated construction of the dispenser 240 allows most manufacturing tolerances of the dispenser 240 to be lowered, and the manufacturing process to be simplified, without effecting the performance and reliability of the dispenser 240. High tolerances are required for only the volume of the pulse chamber 245 and the resilience of the diaphragm 244, since those dimensions affect the resulting PV produced by the dispenser 240. Other dimensions and properties of the dispenser 240 can be relatively relaxed to reduce the costs of the dispenser. For example, in the embodiment shown, at least one of the second and the third layers 254, 256 defines a recess 260 receiving the diaphragm 244. The recess 260 has a depth about equal to a thickness of the diaphragm 244 such that the diaphragm is secured in a substantially fluid-tight manner between the second and the third layers 254, 256. However, a length and a width of the recess 260 are greater than a length and a width of the diaphragm 244 in order to decrease the required manufacturing tolerances of the dispenser 240.

Manufacturing the dispenser 240 is preferably a "drop down" process. First the layers 252, 254, 256 are individually formed with the necessary openings, groove, and recesses. The first layer 252 is then laid down and the valves 241, 242 are dropped into recesses (not shown) in the first layer and correctly positioned within the groove 250. Then the second layer 254 is placed on the first layer 252, and the diaphragm 244 is placed in the recess 260 of the second layer. Finally, the third layer 256 is positioned over the diaphragm 244 and the second layer 254. The layers 252, 254, 256 can be made from a suitably strong and rigid material such as plastic or stainless steel, and can be secured together in a suitable manner, such as with adhesives or by welding. The diaphragm 244 can be made from a suitably expandable yet resilient material, such as rubber or a synthetic rubber.

Figure 5A:
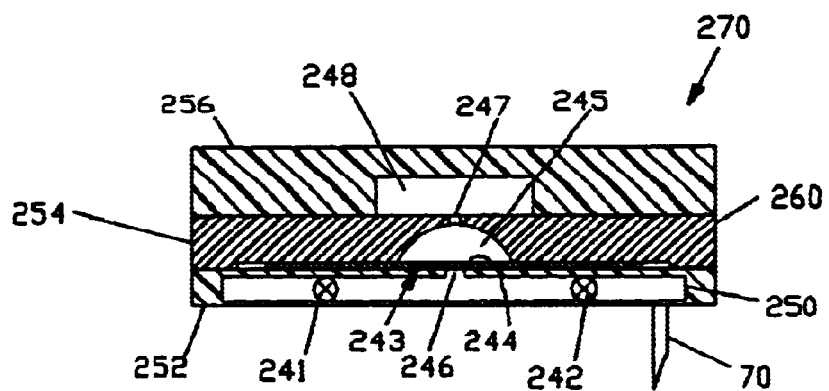
FIGS. 5a and 5b are sectional views of an additional dispenser constructed in accordance with the present invention, illustrating operation of the dispenser.
Figure 5B:
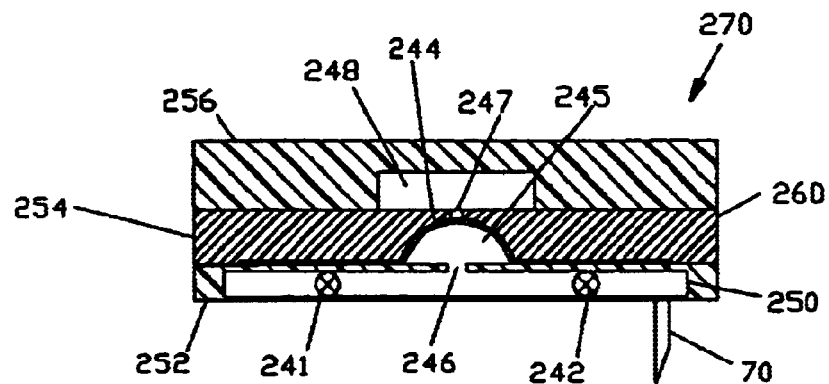

Referring to FIGS. 5a and 5b, another dispenser 270 according to the present invention is shown. The dispenser 270 is similar to the dispenser 240 of FIGS. 4a and 4b such that similar elements have the same reference numerals. A first layer 252 defines the passageway 250 connected to the exit port assembly 70 and an opening 246 in fluid communication with the passageway. The resilient diaphragm 244 is received on the first layer 252 covering the opening 246, and a second layer 254 is received over the diaphragm 244 on the first layer. The second layer 254 has a pulse chamber 245 over the diaphragm 244 and in alignment with the opening 246 of the first layer 252, and a relief port 247 in fluid communication with the pulse chamber 245. A third layer 256 is received on the second layer 254 and defines a relief chamber 248 in fluid communication with the relief port 247 of the second layer 252. The relief chamber 248 allows the pulse chamber 245 to be evacuated upon expansion of the diaphragm 244, yet keeps the pulse chamber sealed and the relief port protected. The relief chamber 248 can also be pressurized to further regulate the PV produced by the dispenser 270.

Figure 6:
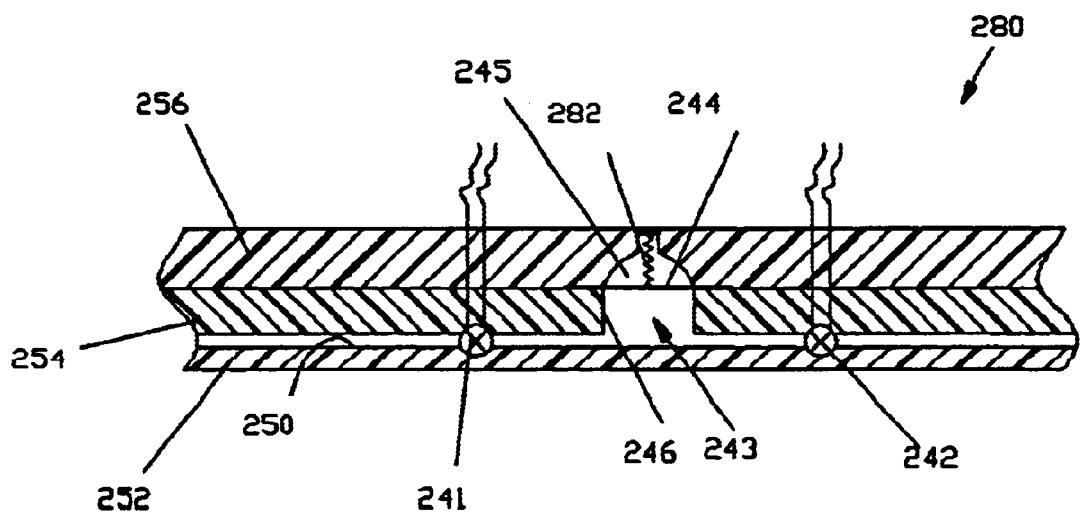
FIG. 6 is a sectional view of an additional embodiment of a dispenser constructed in accordance with the present invention.

FIG. 6 shows another dispenser 280 according to the present invention. The dispenser 280 is similar to the dispenser 240 of FIGS. 4a and 4b such that similar elements have the same reference numerals. The dispenser 280, however, further includes a compression spring 282 biasing the diaphragm 244 away from the pulse chamber 245. The strength of the spring is set along with the volume of the pulse chamber 245 and the resilience of the diaphragm 244, to provide a predetermined PV.

FIGS. 7 through 11a and 11b show an entire fluid delivery device 290 incorporating the laminated construction provided by the present invention. The device 290 is similar to the device of FIGS. 1 and 2, but includes a first layer 252 and a resilient diaphragm 288 received on a surface of the first layer. The surface of the layer 252 has a recess and a groove extending from the recess to the exit port assembly 70, such that the recess of the layer 252 and a portion 244 of the diaphragm 288 define the expandable accumulator 243, and the groove of the layer 252 and the diaphragm 288 define the passageway 250 connected to the exit port assembly 70.

Figure 7:
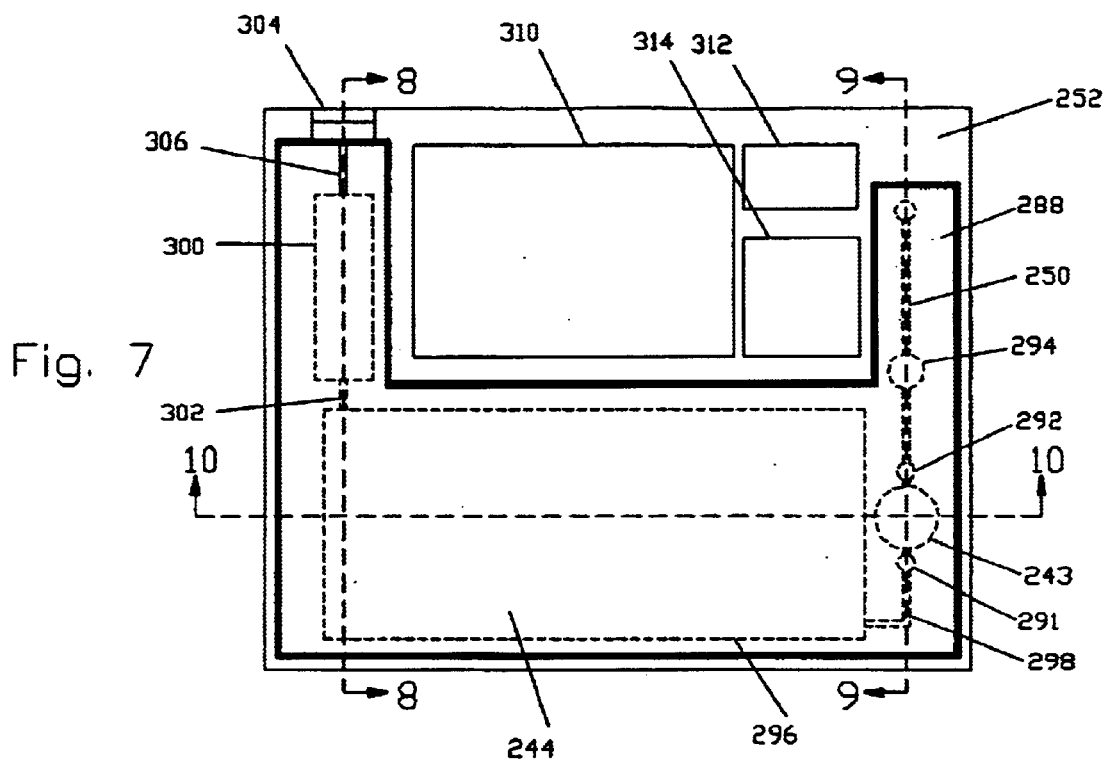
FIG. 7 is a top plan view of a portion of fluid delivery device constructed in accordance with the present invention.

As shown best on FIG. 7, the surface of the first layer 252 also has a valve seat 292 in the groove and an occlusion sensor recess 294 in the groove, between the valve seat 292 and the exit port assembly 70. The surface of the first layer 252 further includes a reservoir recess 296, a groove 298 extending between the reservoir and the accumulator 243, and a valve seat 291 in the groove 298. In addition, the surface of the first layer 252 includes a bubble removal bay 300, a groove 302 extending between the bubble removal bay 300 and the reservoir recess 296, a fill port recess 304, and a groove 298 extending between the fill port recess 304 and the bubble removal bay 300.

Figure 8:
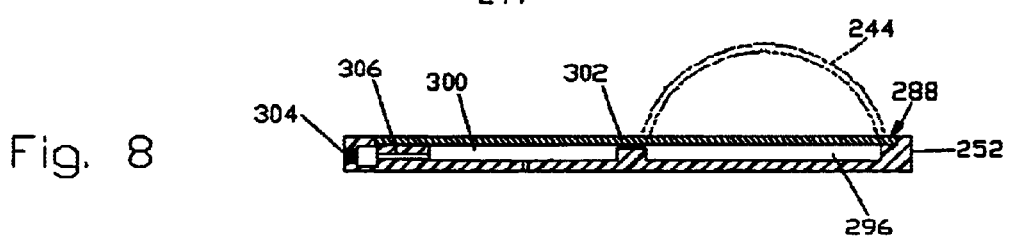
FIG. 8 is a sectional view of the portion of the fluid delivery device taken along line 8—8 of FIG. 7.
Figure 9:
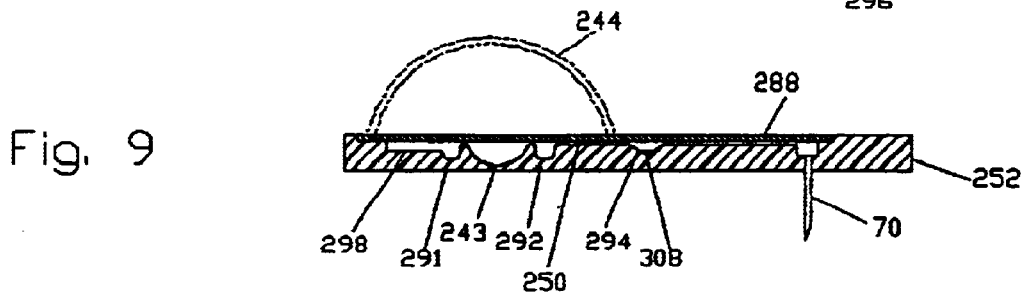
FIG. 9 is a sectional view of the portion of the fluid delivery device taken along line 9—9 of FIG. 7.
Figure 10:
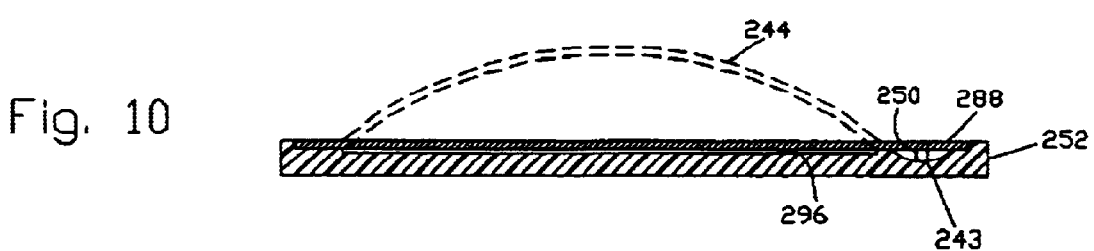
FIG. 10 is a sectional view of the portion of the fluid delivery device taken along line 10—10 of FIG. 7.

As also shown in FIGS. 8 through 11a and 11b, the diaphragm 288 and the first layer 252, therefore, define an occlusion sensor chamber 294, the reservoir 296, a bubble removal chamber 300, and connecting passageways 298, 302, 306. In between the recesses and grooves, the diaphragm 288 is secured to the surface of the layer 252 in a fluid-tight manner, such as with an adhesive. As best shown in FIGS. 8 through 10, the portion 244 of the diaphragm 288 expands when the reservoir 296 is filled in order to pressurize the fluid within the reservoir. In addition, upon the incidence of an occlusion, fluid backs up in the occlusion sensor chamber 294 and causes the portion of the diaphragm 288 over the chamber 294 to expand and increase pressure within the chamber. A switch 308 is positioned in the chamber 294 to monitor for an occlusion, as shown in FIG. 9. The switch 308 is arranged such that when that portion of the diaphragm 288 over the chamber 294 expands, the switch closes to indicate an occlusion. Alternatively, a strain gage can be attached to that portion of the diaphragm 288 over the chamber 294, or a pressure sensor can be positioned in the chamber 294 to monitor for an occlusion.

The diaphragm 288 can be provided with consistent properties, such as resilience, throughout, or can include inconsistent properties. For example, the portion 244 of the diaphragm 288 over the reservoir recess 296 can be provided with a greater thickness to increase the resilience of that portion, while the thickness of the diaphragm 288 over the valve seats 291, 292 may be made thinner to decrease the resilience of those portions. In addition, the diaphragm 288 can be made from a material that allows gas to pass through yet prevents liquid from passing through, such that the diaphragm 288 also acts as a bubble removal filter. Furthermore, the diaphragm 288 can be provided with coatings. For example, surfaces of the diaphragm 288 in contact with flow paths can be coated with material that promotes flow and avoids precipitation (such as insulin crystallization). The diaphragm 288 can also be coated with lines of conductive material, for example, to support transmission of electrical signals between the local processor and other components of the device.

Figure 11A:
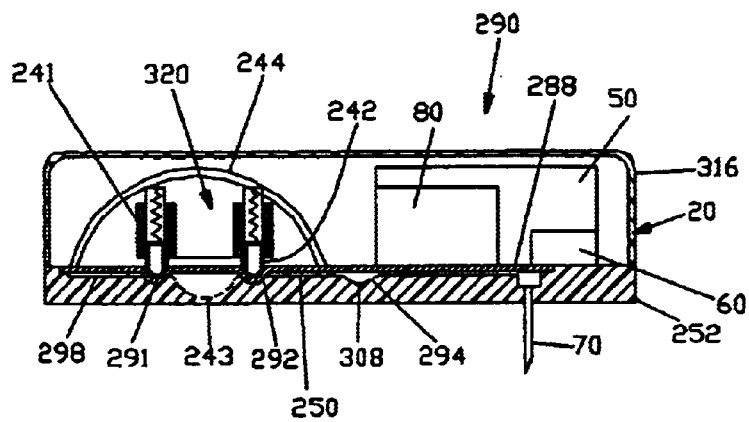
FIGS. 11a and 11b are sectional views of the entire fluid delivery device of FIG. 7, illustrating operation of the device.
Figure 11B:
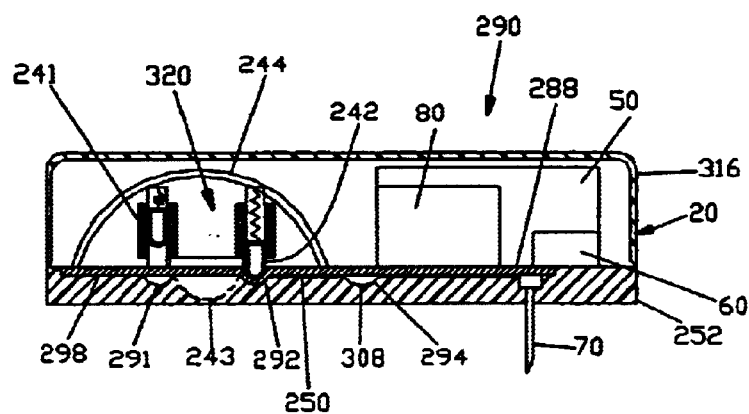

As shown in FIG. 7, the first layer 252 also defines recesses 310, 312, 314, which are not covered by the diaphragm 288, for other components of the device including the local processor 50, the wireless communication unit 60 and the battery 80. FIGS. 11a and 11b show a cover 316 attached to the first layer 252 to complete the housing 20 of the fluid deliver device 290. The cover 316 contains the power source 80, the wireless communication unit 60 and the local processor 50 of the device 290. The cover 316 also includes the inlet and the outlet valves 241, 242 aligned over the valve seats 291, 292 of the first layer 252. The valves 241, 242 and the accumulator 243 comprise the dispenser 320 for use with the pressurized reservoir 296. As shown, the cover 316 also provides an enclosed space that allows for expansion of the diaphragm portion 244 over the reservoir 296.

Figure 12A:
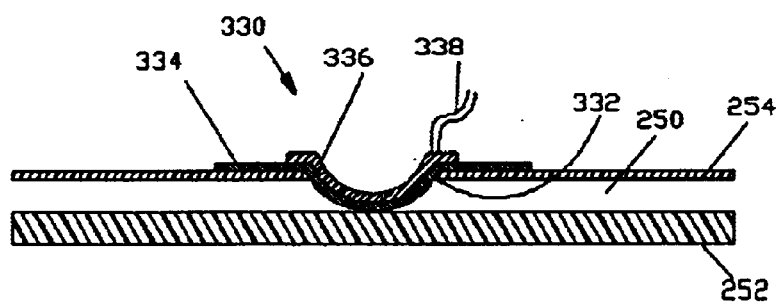
FIGS. 12a and 12b are sectional views of an embodiment of a valve constructed in accordance with the present disclosure, illustrating operation of the valve.
Figure 12B:
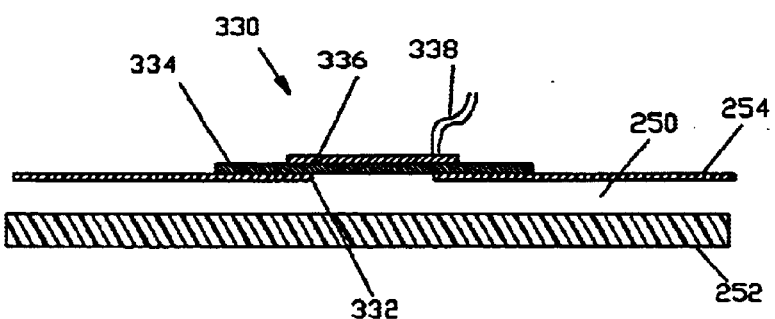

FIGS. 12a and 12b show a valve 330 constructed in accordance with the present invention for use as part of a laminated dispenser or part of a laminated fluid delivery device. The valve 330, for example, can comprise the inlet valve of the dispenser controlling flow from a reservoir into the accumulator. The valve 330 is part of a passageway 250 formed from first and second layers 252, 254, wherein the second layer 254 includes an opening 332 communicating with the passageway. The valve 330 includes a layer of resilient fluid-tight material 334 covering the opening, and a layer of piezoelectric material 336 covering the layer of resilient fluid-tight material.

The layers of resilient fluid-tight material 334 and piezoelectric material 336 are arranged such that upon contracting, the layer of piezoelectric material 336 forces the layer of resilient fluid-tight material 334 into the opening 332 of the passageway 250 and substantially closes the passageway, as shown in FIG. 12a. As shown, the piezoelectric material 336 includes a wire 338 for connection to a power source (not shown). When power is applied to the piezoelectric material 336, the piezoelectric material straightens out, thereby opening the passageway 250, as shown in FIG. 12b. The resilient fluid-tight material 334 can be provided as part of the resilient diaphragm forming the accumulator of the dispenser. In the preferred embodiment, the piezoelectric material 336 is normally curved when de-energized, and deforms to a straight geometry when energized, such that the passageway 250 is normally closed.

Figure 13A:
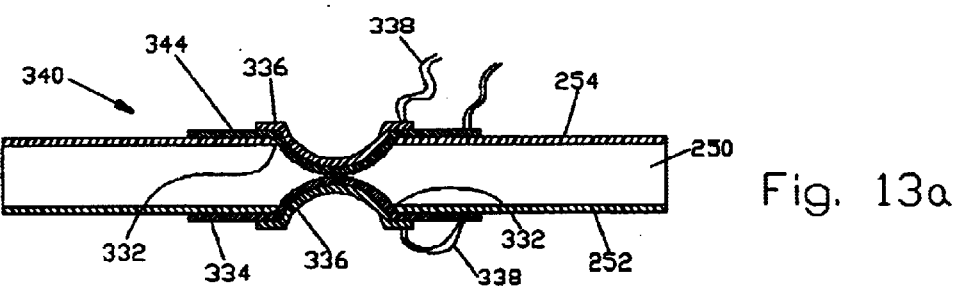
FIGS. 13a and 13b are sectional views of another embodiment of a valve constructed in accordance with the present disclosure, illustrating operation of the valve.
Figure 13B:
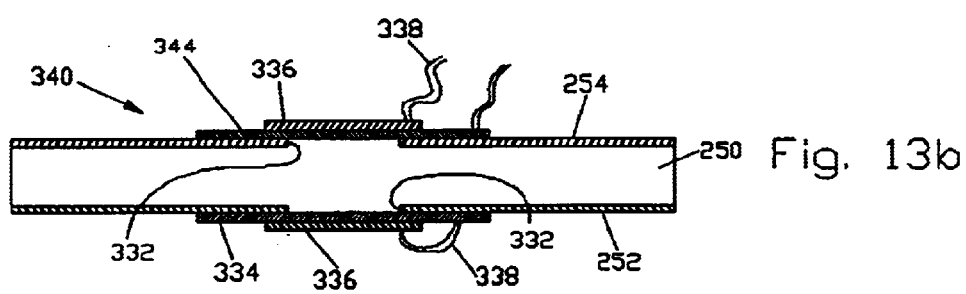

FIGS. 13a and 13b show another valve 340 constructed in accordance with the present invention. The valve 340 is similar to the valve 330 of FIGS. 12a and 12b such that similar elements have the same reference numerals. The valve 340 of FIGS. 13a and 13b, however, further includes an opening 332 in the first layer 252, and a layer of resilient fluid-tight material 334 covering the opening in the first layer, and a layer of piezoelectric material 336 covering the layer of resilient fluid-tight material. As shown, the layers of piezoelectric material 336 react together to close the passageway 250 when de-energized (FIG. 13a), and to open the passageway when energized (FIG. 13b). An alternative embodiment can include a tubular layer of resilient fluid-tight material and a tubular layer of piezoelectric material positioned over an annular opening in the passageway.

Figure 14:
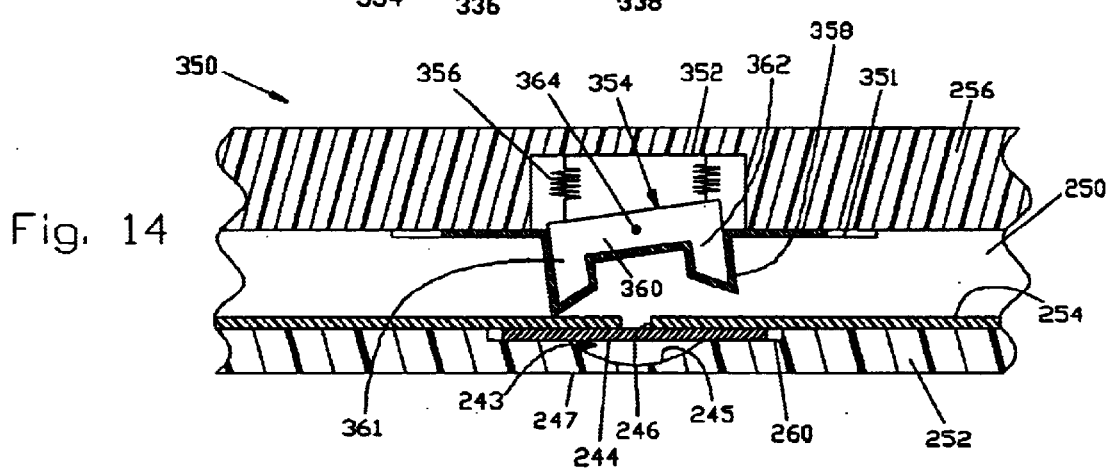
FIG. 14 is a sectional view of a further embodiment of a valve constructed in accordance with the present disclosure.

A valve assembly 350 constructed in accordance with the present invention is shown in FIG. 14. The valve assembly 350 is shown as part of a laminated dispenser having first, second and third layers 252, 254, 256. The first layer 252 defines the pulse chamber 245, the evacuation port 247, and the enlarged recess 260 receiving the diaphragm 244 over the pulse chamber to form the accumulator 243. The second layer 254 defines the groove for the passageway 250, an opening 246 communicating with the groove in alignment with the pulse chamber 245, and a recess 351 on the surface of the second layer 254 in alignment with the opening. The third layer 256 defines a valve assembly chamber 352 facing the second layer 254 in alignment with the recess 351 of the second layer.

The valve assembly 350 includes a valve member 354, springs 356 and a fluid resistant cover 358. The valve member 354 is received in the valve assembly chamber 352 of the third layer 256 and includes a bar 360 extending parallel with the passageway 250 and pivotally mounted on the third layer about a pivot point 364 aligned with the accumulator 243. An inlet valve 361 and an outlet valve 362 extend from the bar 360 into the passageway 250 on opposite sides of the pivot point 364 (and on opposite sides of the accumulator 243). The springs 356 are positioned between the ends of the bar 360 and the third layer 256 to bias each end towards the second layer 254. The fluid resistant cover 358 is received in the recess 351 of the second layer 254 (the recess preferably being oversized with respect to the cover to reduce manufacturing tolerances), and provides a water-tight seal between the passageway 250 and the valve assembly 350.

Although not shown, the valve assembly 350 also includes an actuator for causing the valve member 354 to pivot. The actuator can comprise a rotary motor, a linear motor, a clock spring, and piezoelectric material, for example. Many different types of actuators can be used for causing the valve member 354 to pivot when desired. The pivoting valve assembly 354 provides the benefit of the valves 361, 362 alternatively blocking the passageway 250 at all times, such that unregulated flow to the exit port assembly is not permitted. As shown in FIG. 14, the valve assembly 350 also utilizes "drop down" construction, wherein all elements of the valve assembly are assembled from above the second layer 254, to simplify manufacturing.

Figure 15:
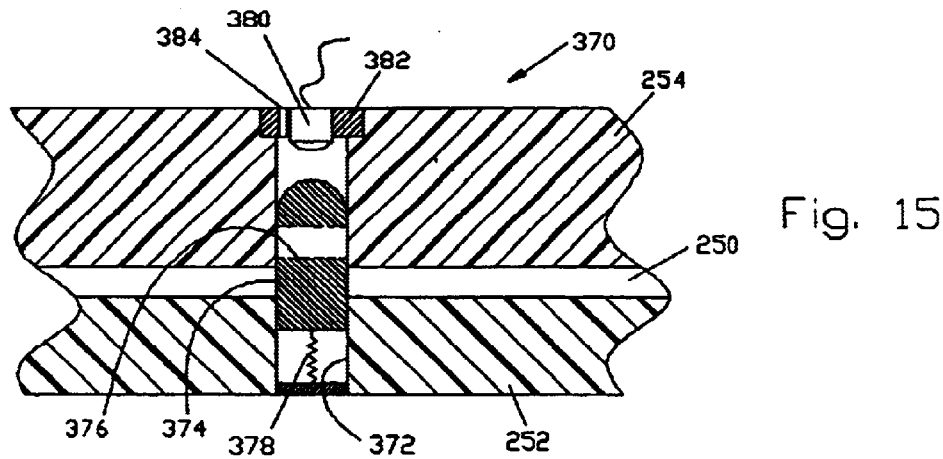
FIG. 15 is a sectional view of another embodiment of a valve constructed in accordance with the present disclosure.

Another valve assembly 370 constructed in accordance with the present invention is shown in FIG. 15. The valve assembly 370 is shown as part of a laminated dispenser having first and second layers 252, 254, with the passageway 250 defined between the layers. The laminated layers 252, 254 also define a bore 372 bisecting the passageway 250 and receiving the valve assembly 370.

The valve assembly 370 includes a valve member 374 movably received in the bore 372 and including an opening 376, and a spring 378 biasing the valve member such that the opening 376 of the valve member is normally offset from the passageway 250 and the passageway is blocked by the valve member 374. The assembly 370 also includes an actuator 380 for moving the valve member 374 upon being actuated such that the opening 376 of the valve member 374 aligns with the passageway 250 to thereby allow flow through the passageway. In the embodiment shown, the actuator comprises a gas generator 380 for pressurizing the bore 372 upon being actuated. The gas generator 380 is mounted in a plug 382 fitted in the second layer 254 and having a gas release port 384 communicating with the bore 372. As shown in FIG. 15, the valve assembly 370 also utilizes "drop down" construction, wherein all elements of the valve assembly can be assembled from above the second layer 254, to simplify manufacturing.

During operation, the actuated gas generator 380 pressurizes the bore 372 above the valve member 374 and forces the valve member to move against the spring 378, so that the opening 376 aligns with the passageway 250 and opens the passageway. The gas release port 384 allows a predetermined rate of gas to exit the bore 372 in order to limit the total pressure in the bore and allow a controlled decay of pressure. In one embodiment, the valve assembly 370 is positioned near the exit port assembly of a fluid delivery device to limit the useable life of the fluid delivery device. For example, the fluid delivery device can include automatic or manual means for actuating the gas generator 380 upon the device being secured to a patient's skin, and the gas generator can be provided with enough fuel to maintain the valve member 374 open for three days. When the fuel in the gas generator 380 is depleted, the valve member 374 closes and the fluid delivery device must be replaced with a new device. The valve 370 can also be used to pulse fluid as long as the gas generation rate of the gas generator 380 and the gas release rate of the gas release port 384 have time constants slightly smaller than the maximum pulse rate.

Figure 16:
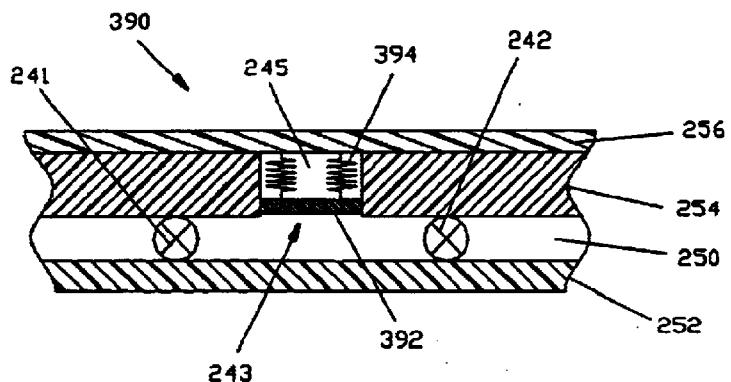
FIG. 16 is a sectional view of another embodiment of a dispenser constructed in accordance with the present invention.

Referring now to FIG. 16, another laminated dispenser 390 constructed in accordance with the present invention is shown. The dispenser 390 is for use with a pressurized reservoir and includes an inlet valve 241, an accumulator 243 and an outlet valve 242. The dispenser includes three layers 252, 254, 256. The second and the first layers 252, 254 define the passageway 250 connected to the exit port assembly, and the second layer 254 defines the pulse chamber 245 communicating with the passageway.

A piston 392 is slidingly received in the pulse chamber 245, and a substantially fluid tight seal is provided between the piston and the wall of the pulse chamber. The piston 392 in effect comprises the expandable membrane of the accumulator 243. The third layer 256 is received on the second layer 254 and closes the pulse chamber 245, and springs 394 are positioned between the third layer and the piston 392 and bias the piston away from the third layer. During operation, the outlet valve 242 is closed and the inlet valve 241 is opened to allow pressurized fluid from the reservoir to move the piston 392 against the springs 392 and into the pulse chamber 245 to expand the accumulator 243 by the predetermined pulse volume. Then the inlet valve 241 is closed and the outlet valve 242 is opened such that the biased piston 392 can force the pulse volume of liquid to the exit port assembly.

Figure 17A:
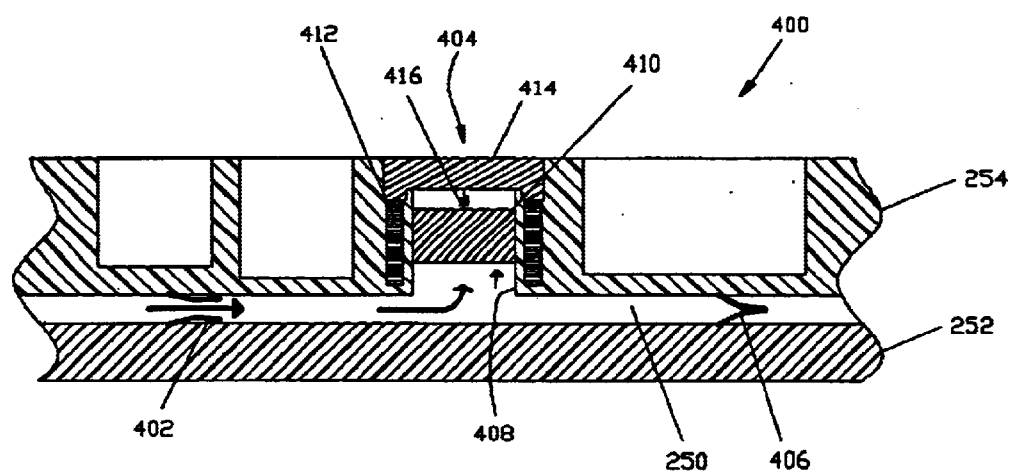
FIGS. 17a and 17b are sectional views of another embodiment of a dispenser constructed in accordance with the present disclosure, illustrating operation of the dispenser.
Figure 17B:
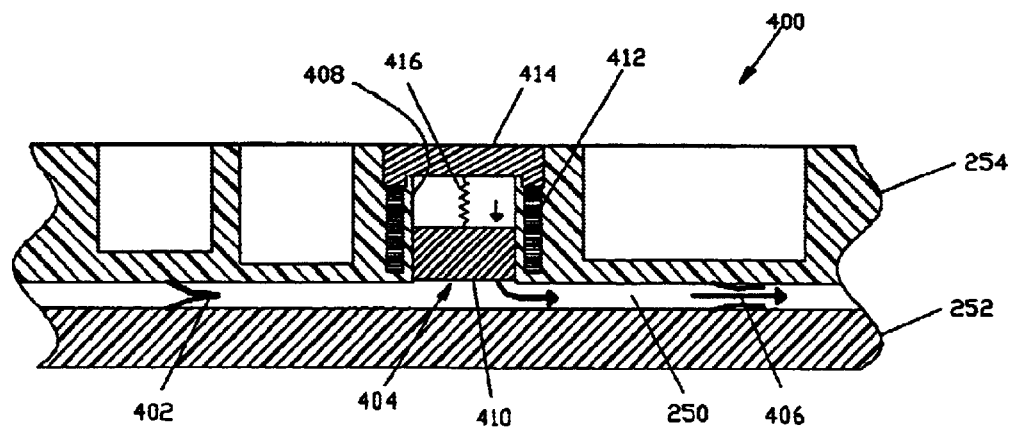

Referring to FIGS. 17a and 17b, an additional laminated dispenser 400 constructed in accordance with the present invention is shown. The dispenser 400 is for use with a non-pressurized reservoir (not shown) and, therefore, is designed to act as a pump instead of simply a regulator. The dispenser 400 includes an inlet valve 402, an accumulator 404, and an outlet valve 406. The valves 402, 406 comprise one-way valves, such as duckbill valves, and the accumulator 404 is an "active" accumulator, as opposed to the "passive" accumulators used in the previously described dispensers.

The second and the first layers 252, 254 of the dispenser 400 define the passageway 250 connected between the reservoir and the exit port assembly, and the second layer 254 defines a bore 408 communicating with the passageway 250. A piston 410 is slidingly received in the bore 408 and acts as the expandable membrane of the accumulator 404. The dispenser 400 also includes an actuator 412 for moving the piston 410 in the bore 408 to draw fluid from the reservoir through the inlet valve 402 (the one-way outlet valve 406 prevents fluid from being draw though the outlet valve 406) and expel liquid through the outlet valve 406 to the exit port assembly (the one-way inlet valve 402 prevents fluid from being expelled though the inlet valve 402).

In the embodiment show, the actuator comprises a magnetic coil 412 received in an annular groove provided in the second layer 254, coaxial with the piston 410, which is made from magnetic material. A plug 414 seals the piston 410 and the coil 412 in the second layer 254, such that the portion of the bore 408 between the piston 410 and the plug 414 comprises the pulse chamber of the accumulator 404. The dispenser 400 includes a coiled compression spring 416 positioned between the plug 414 and the piston 410 biasing the piston towards the passageway 250. The coil 412 is arranged to bias the piston 410 against the spring 416 upon being energized.

During operation of the dispenser 400, the coil 412 is energized such that movement of the piston 410 expands the accumulator 404, and draws fluid from the reservoir, through the one-way inlet valve 402 and into the bore 408, as shown in FIG. 17a. The one-way inlet valve 402 closes when the accumulator 404 is fully expanded. Then the coil 412 is de-energized, so that the spring 416 is allowed to push the piston 410 back towards the passageway 250, compress the accumulator 404, and expel the liquid through the one-way outlet valve 406 to the exit port assembly, as shown in FIG. 17b.

Figure 18A:
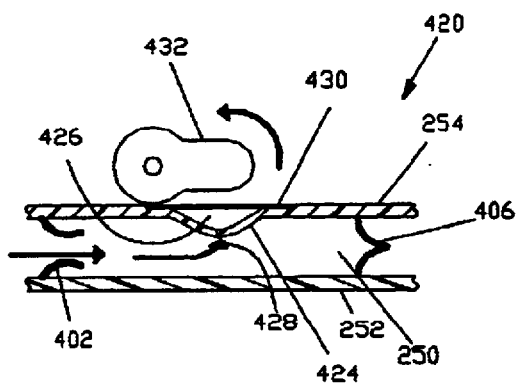
FIGS. 18a and 18b are sectional views of another embodiment of a dispenser constructed in accordance with the present disclosure, illustrating operation of the dispenser.
Figure 18B:
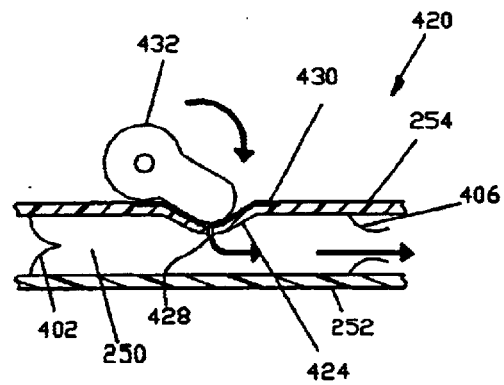

FIGS. 18a and 18b, show another laminated dispenser 420 constructed in accordance with the present invention, and which operates in a manner similar to the dispenser 400 of FIGS. 17a and 17b. The dispenser 420 includes a one-way inlet valve 402, an "active" accumulator 424, and a one-way outlet valve 406. The second and the first layers 252, 254 of the dispenser 420 define the passageway 250 connected between the reservoir (not shown) and the exit port assembly (not shown).

The accumulator 424 includes a pulse chamber 426 formed in a surface of the second layer 254 facing away from the first layer 252, and an opening 428 providing fluid communication between the pulse chamber 426 and the passageway 250. A resilient diaphragm 430 is received on the second layer 254 and covering the pulse chamber 426 in a fluid-tight manner.

The dispenser 420 also includes an actuator 432 for pushing the diaphragm 430 into the pulse chamber 426 to reduce the volume of the accumulator 424 and produce a pulse volume. In the embodiment shown, the actuator comprises a rotatable cam 432 and a motor (not shown) or other rotational device for rotating the cam. During operation, the cam 432 is rotated away from the diaphragm 430 such that the diaphragm expands the accumulator 424, and draws fluid from the reservoir, through the inlet valve 402 and into the pulse chamber 426, as shown in FIG. 18a. The inlet valve 402 closes when the accumulator 424 is fully expanded. Then the cam 432 is rotated back into the diaphragm 430, so that the diaphragm compresses the pulse chamber 426 and expels the liquid through the outlet valve 406 to the exit port assembly, as shown in FIG. 18b.

Figure 19A:
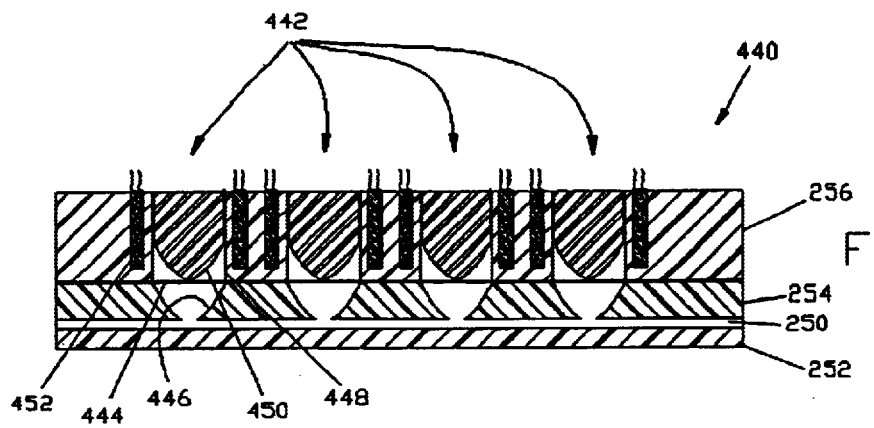
FIGS. 19a and 19b are sectional views of another embodiment of a dispenser constructed in accordance with the present disclosure, illustrating operation of the dispenser.
Figure 19B:
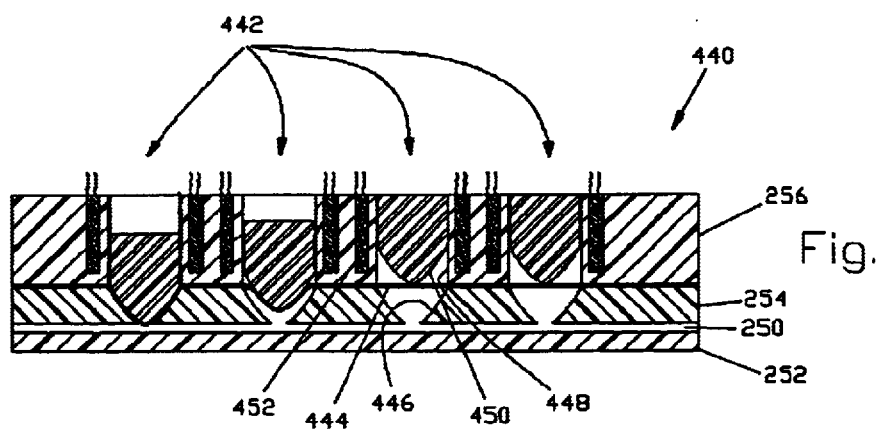

Referring to FIGS. 19a and 19b, an additional laminated dispenser 440 constructed in accordance with the present invention is shown. The dispenser 440 is for use with a non-pressurized reservoir (not shown) and, therefore, is designed to act as a pump instead of simply a regulator. The dispenser 440 includes a plurality of "active" accumulators 442 and no inlet valve or outlet valve. The accumulators 442 are arranged successively with respect to the passageway 250 and operate one after another such that the dispenser 440 operates as a linear peristaltic pump.

The second and the first layers 252, 254 of the dispenser 440 define the passageway 250 connected between the reservoir and the exit port assembly. The resilient diaphragm 444 is positioned between the second layer 254 and the third layer 256 in a liquid-tight manner. For each accumulator 442, the second layer 254 defines a pulse chamber 446 communicating with the passageway 250, and the third layer 256 defines a bore 448 aligned with the pulse chamber.

The dispenser 440 also includes actuators for compressing the pulse chambers 446 and expelling pulse volumes of liquid towards the exit port assembly. In the embodiment shown, the actuators comprise pistons 450 made from magnetic material and slidingly received in the bores 448, and magnetic coils 452 received in annular grooves provided in the third layer 256, coaxial with the pistons 450. Each coil 452 is arranged such that, upon being energized, the coil 452 forces the piston 450 against the diaphragm 444 to collapse the pulse chamber 446 and expel a pulse volume of fluid from the accumulator 442 into the passageway 250. Upon being de-energized, the coil 452 releases the piston 450 and allows the diaphragm 444 to push the piston back, and draw a pulse volume of fluid into the pulse chamber 446. During operation of the dispenser 440, the coils 452 are successively energized and de-energized so that fluid is drawn from the reservoir, expelled and drawn successively into the accumulators 442, and expelled to the exit port assembly. Preferably, at least one of the pistons 450 is always in a closed position to occlude the fluid path and prevent the free flow of fluid through the passageway to the exit port assembly. In an alternative embodiment, the pistons 450 can be biased closed, with a spring, and the coils 452 arranged to pull the pistons away from the passageway when energized.

Figure 20A:
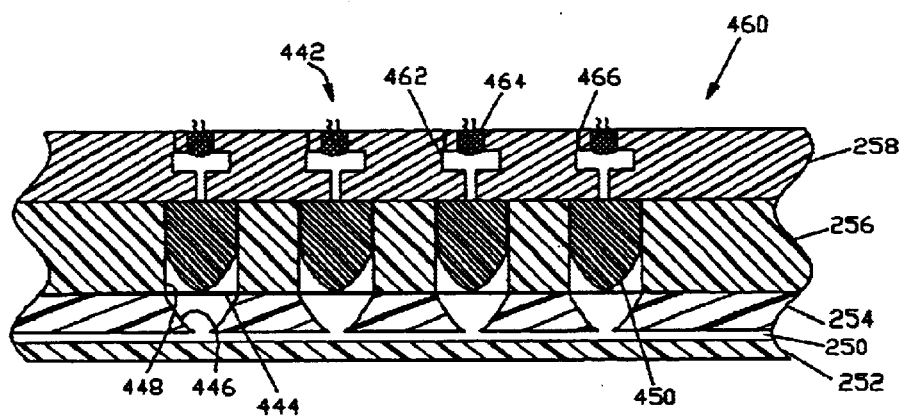
FIGS. 20a and 20b are sectional views of a further embodiment of a dispenser constructed in accordance with the present disclosure, illustrating operation of the dispenser.
Figure 20B:
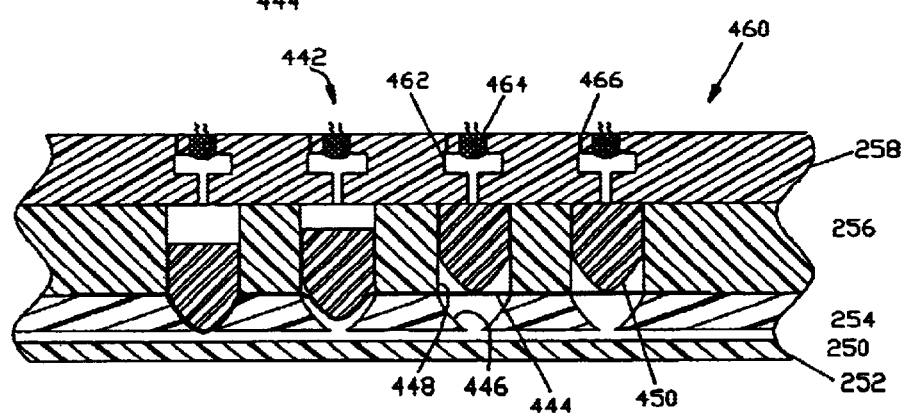

FIGS. 20a and 20b show another laminated dispenser 460 according to the present invention. The dispenser 460 is similar to the dispenser 440 of FIGS. 19a and 19b, but includes a fourth layer 258 defining bores 462 aligned with the bores 448 of the third layer 256. In addition, the actuators comprise the pistons 450, and gas generators 464 received in the bores 462 of the fourth layer 258. The gas generators 464 pressurize the bores 448, 462 and biasing the piston 450 against the diaphragm 444 upon being actuated. The fourth layer 258 also includes gas release ports 466 communicating with the bores 462.

Figure 21A:
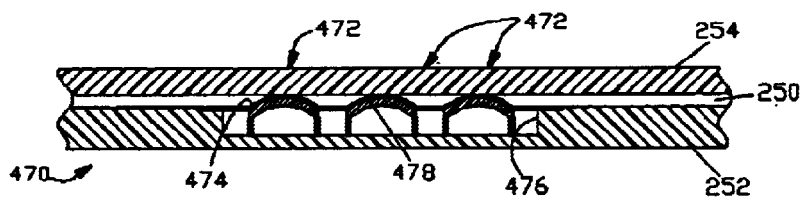
FIGS. 21a, 21b and 21c are sectional views of another embodiment of a dispenser constructed in accordance with the present disclosure, illustrating operation of the dispenser.
Figure 21B:
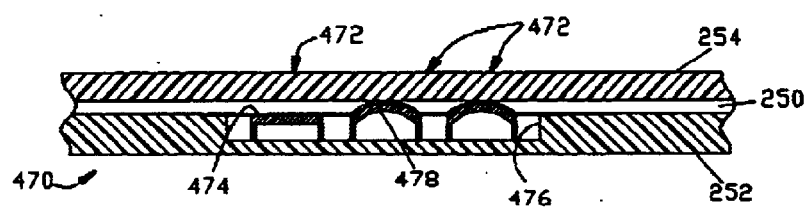
Figure 21C:
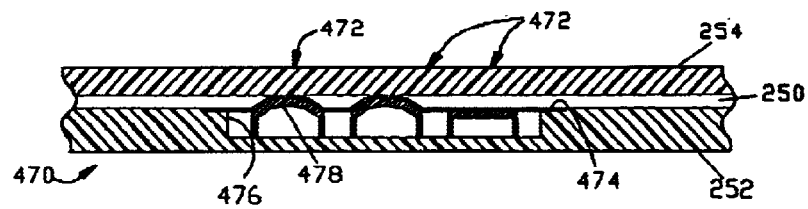

Referring to FIGS. 21a, 21b, and 21c, a further embodiment of a laminated dispenser 470 constructed in accordance with the present invention is shown. The dispenser 470 is also for use with a non-pressurized reservoir and acts as a pump instead of simply a regulator. The dispenser 470 includes a plurality of "active" accumulators 472 and no inlet valve or outlet valve. The accumulators 472 are arranged successively with respect to the passageway 250 and operate one after another such that the dispenser 470 operates as a linear peristaltic pump.

The dispenser 470 includes a first layer 252 having a recess 476, with a diaphragm 474 positioned against the surface of the first layer 252. The second layer 254 is received against the diaphragm 474 and includes a surface defining a groove, such that the diaphragm and the groove define the passageway 250 connecting the reservoir to the exit port assembly.

Each accumulator 472 includes an actuator 478. The actuators 478 are successively positioned with respect to the passageway 250 within the recess 476 of the first layer 252. The actuators 478 are arranged to push the diaphragm 474 towards the second layer 254 upon being actuated. The portion of the recess 476 above the diaphragm 474 comprises the pulse chambers of the accumulators 472.

In the embodiment shown, the actuators comprise segments of piezoelectric material 478. Each segment 478 is mounted and arranged such that, when de-energized, the segment 478 normally assumes a curved geometry to push the diaphragm 474 towards the second layer, and when energized, deforms to a straight geometry to allow the diaphragm to return to its original position. In the preferred embodiment all of the piezoelectric elements 478 are normally in a curved state when de-energized, to occlude the passageway 250 and prevent the free flow of fluid through the passageway to the exit port assembly.

Figure 22A:
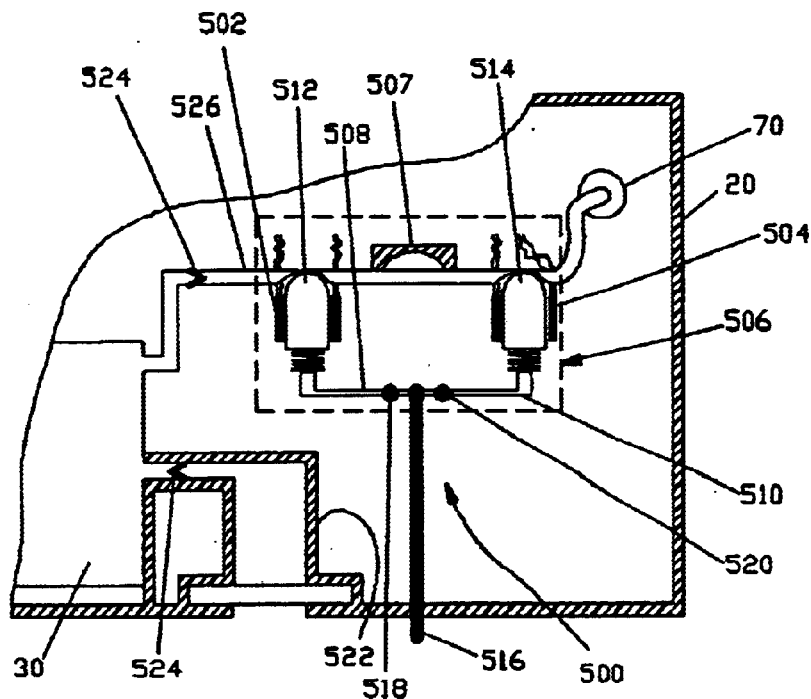
FIGS. 22a and 22b are sectional views of a portion of another embodiment of a fluid delivery device including a priming mechanism constructed in accordance with the present disclosure, and illustrating operation of the priming mechanism.
Figure 22B:
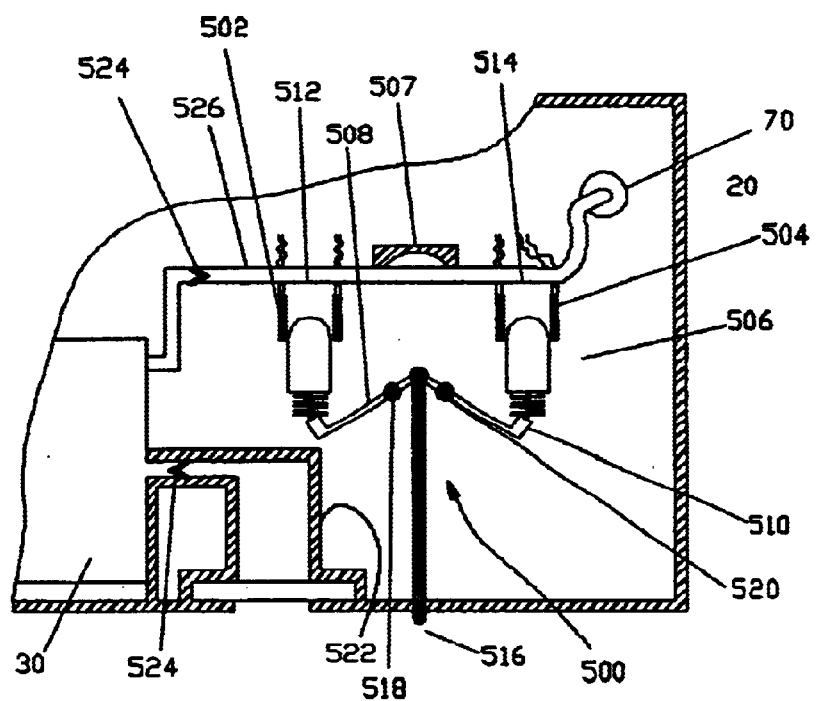

Referring now to FIGS. 22a and 22b, the present invention also provides a priming mechanism 500 for simultaneously maintaining an inlet valve 502 and an outlet valve 504 of a dispenser 506 open, such that fluid can flow through the dispenser (also having an accumulator 507) to the exit port assembly 70 during filling of the reservoir 30. Priming ensures that the entire volume of the fluid delivery passages of the fluid delivery device are filled with fluid prior to operation, so that an accurate volume of fluid can be delivered by the device.

In the specific embodiment shown, the priming mechanism 500 includes a pivotally movable first link 508 operatively connected to the inlet valve 502 such that the inlet valve is opened upon pivoting movement of the first link 508. A pivotally movable second link 510 is operatively connected to the outlet valve 504 such that the outlet valve is opened upon pivoting movement of the second link. The priming mechanism 500 also includes a movable priming rod 516 operatively connected to the first and the second links 508, 510 for pivoting the links upon movement of the rod 516.

As shown, the inlet and the outlet valves 502, 504 each include a valve member 512, 514 movable between open and closed positions. The first link 508 extends between the first valve member 512 and the priming rod 516 and is pivotally movable about a pivot point 518 of the first link located between the valve member 512 and the priming rod. The second link 510 extends between the second valve member 514 and the priming rod 516 and is pivotally movable about a pivot point 520 of the second link located between the valve member 514 and the priming rod. The priming rod 516 is linearly movable to pivot the links 508, 510 and open the valve members 512, 514. The priming rod 516 extends out of the housing 20 of the fluid delivery device, and is depressed into the housing 20 by a user to open the valves 502, 504 prior to filling the reservoir 30 through fill port 522. One-way valves, such as duckbill valves 524, are positioned within the fill port 522 and a passageway 526 of the dispenser 506. FIG. 22b shows a the priming rod 516 depressed into the housing 20 and the valves 502, 504 opened, while FIG. 22a shows the priming rod 516 extending out of the housing 20 and the valves 502, 504 closed.

Figure 23A:
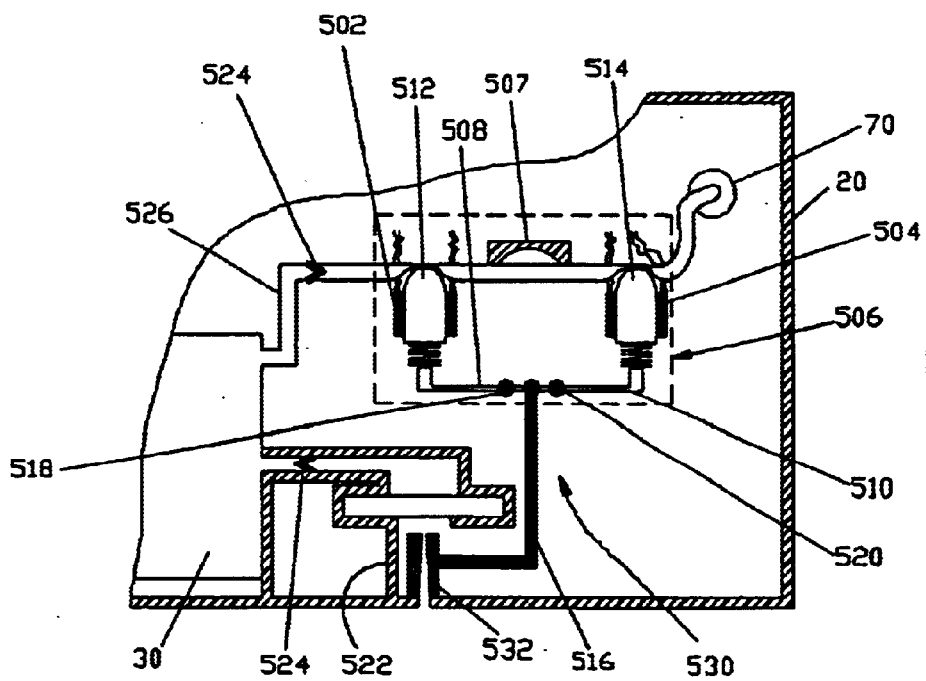
FIGS. 23a and 23b are sectional views of a portion of an additional embodiment of a fluid delivery device including a priming mechanism constructed in accordance with the present disclosure, and illustrating operation of the priming mechanism.
Figure 23B:
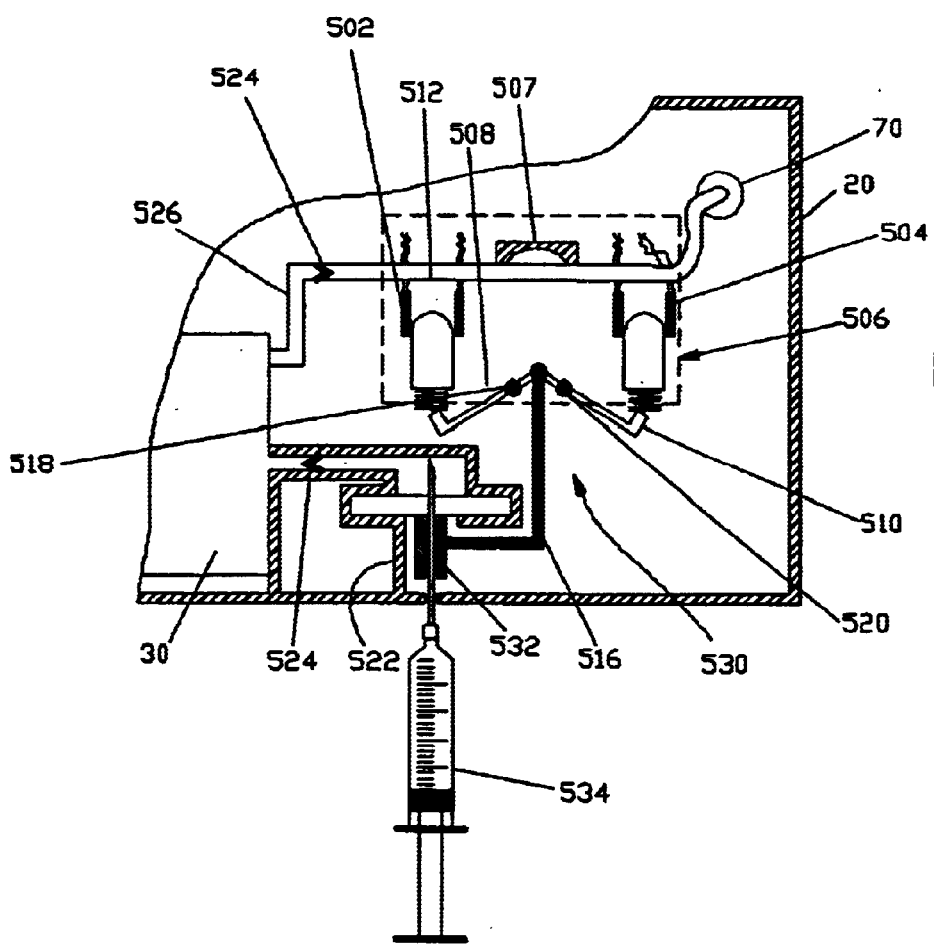

FIGS. 23a and 23b shown another priming mechanism 530 according to the present invention. The mechanism 530 is similar to the mechanism 500 of FIGS. 22a and 22b such that similar elements have the same reference numerals. The mechanism 530, however, further includes a collar 532 connected to the priming rod 516 and received in the fill port 522 of the device. The fill port 522 is connected to the reservoir 30 and adapted for receiving a needle 534 for filling the reservoir. The collar 532 is adapted to frictionally receive the needle 534 inserted into the fill port 522 so that the inserted needle causes movement of the collar 532 and the priming rod 516 and pivoting movement of the links 508, 510. The dispenser valves 502, 504 are therefore opened and the device is primed automatically upon filling of the reservoir 30, shown in FIG. 23b.

Figure 24:
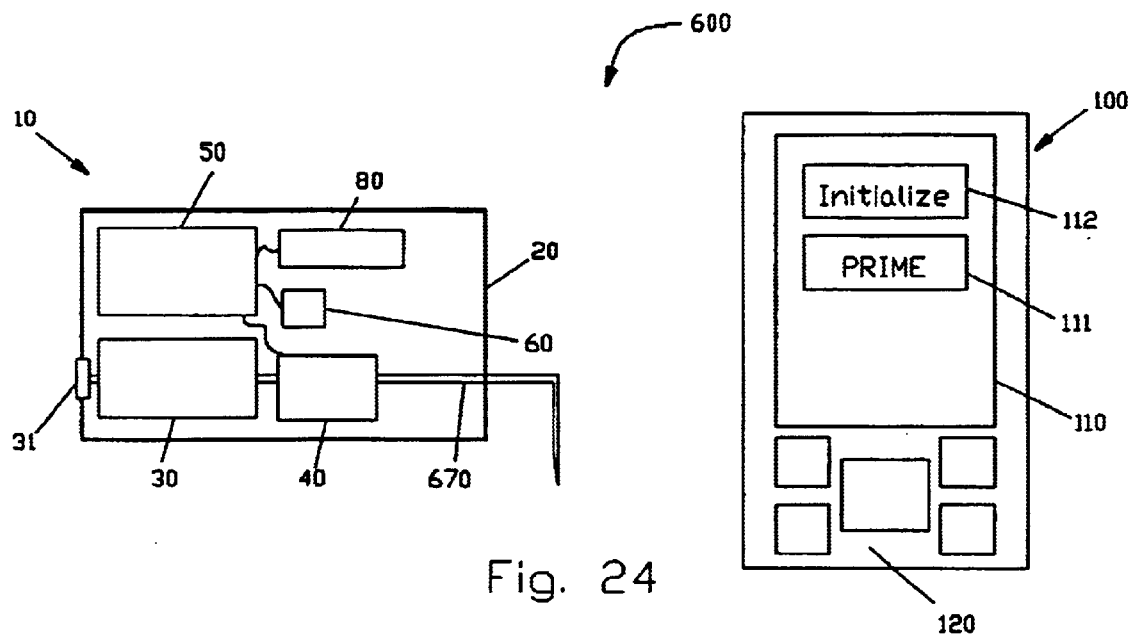
FIG. 24 is a schematic illustration of a further embodiment of a fluid delivery device constructed in accordance with the present disclosure.
Figure 25:
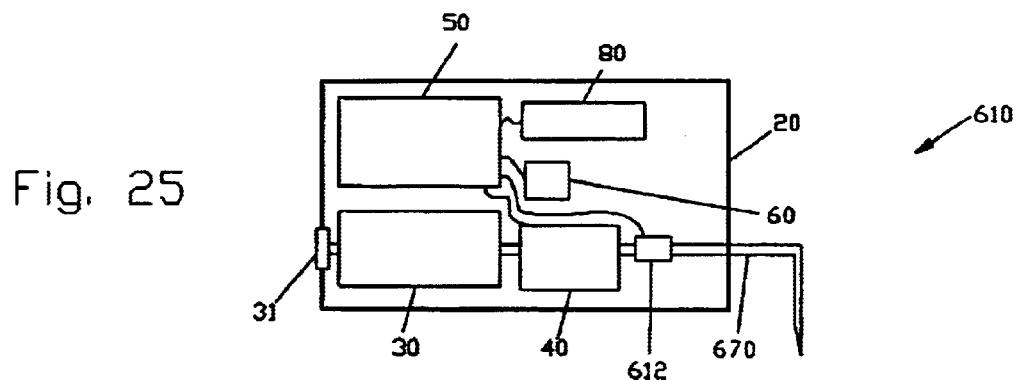
FIG. 25 is a schematic illustration of another embodiment of a fluid delivery device and a remote control device constructed in accordance with the present disclosure.
Figure 26:
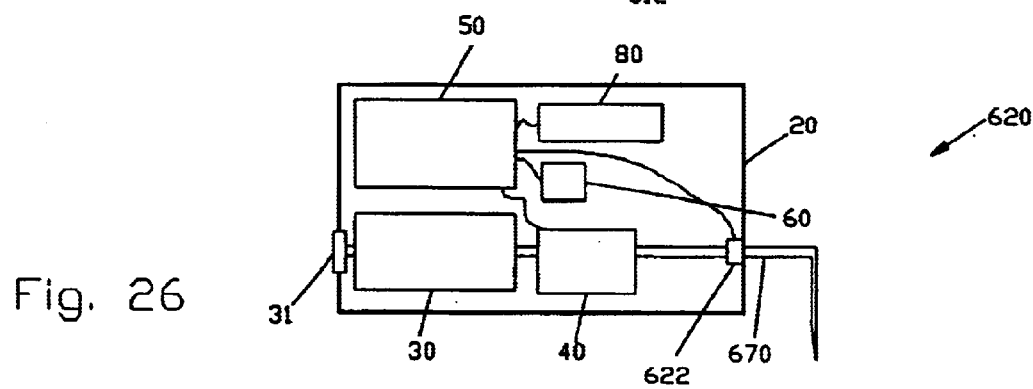
FIG. 26 is a schematic illustration of an additional embodiment of a fluid delivery device constructed in accordance with the present disclosure.

Referring to FIGS. 24 to 26, the present invention also provides fluid delivery devices 10 having automatic priming systems 600, 610, 620. Each device 10 is provided with an exit port assembly comprising an integrated transcutaneous patient access tool 670 having a known internal volume. In the particular embodiments shown, the patient access tool is a needle 670. Because the volume to the tip of the needle 670 is known, the local processor 50 of the device 10 can be programmed to prime the needle 670 automatically.

In the preferred embodiment of FIG. 24, the local processor 50 is programmed to instruct the dispenser 40 to deliver a volume of fluid to the needle 670 equal to the known internal volume of the needle 670. Preferably, the remote controller 100 is provided with a "PRIME" command for a user to select. In the embodiment of the controller 100 illustrated in FIG. 24, a prime command button 111 is shown provided on a touch screen 110 after an "INITIALIZE" command 112. When the prime command 111 is selected, the remote controller 100 communicates with the fluid delivery device 10 and instructs the local processor 50 to prime the needle 670.

The fluid delivery device 610 of FIG. 25 further includes a flow sensor 612 arranged to provide a signal to the local processor 50 indicative of the volume of fluid passing from the dispenser 40 to the needle 670. The local processor 50 is programmed to prime the needle 670 by instructing the dispenser 40 to deliver fluid until the flow sensor 612 indicates to the local processor that a volume of fluid equal to the known internal volume of the needle 670 has been delivered to the needle. The local processor 50 is also programmed to utilize the signals from the flow sensor 612 to monitor the needle 670 for occlusions once the needle has been primed.

The device 620 of FIG. 26 is similar to the device 600 of FIG. 24, but further includes a fluid detector 622 positioned between the dispenser 40 and the needle 670 for providing a signal to the local processor 50 indicative of fluid passing into the needle 670. The local processor 50 is programmed to prime the needle 670 by instructing the dispenser 40 to deliver fluid for a predetermined period and at a predetermined flow rate after receiving an initial indication from the fluid detector 622 that fluid has reached the fluid detector 622. In addition, the local processor 50 can be programmed to provide a signal that air has been detected in the fluid path when the fluid detector 622 stops indicating the presence of fluid upon operation of the dispenser 40 and after the needle 670 has been primed.

Figure 27:
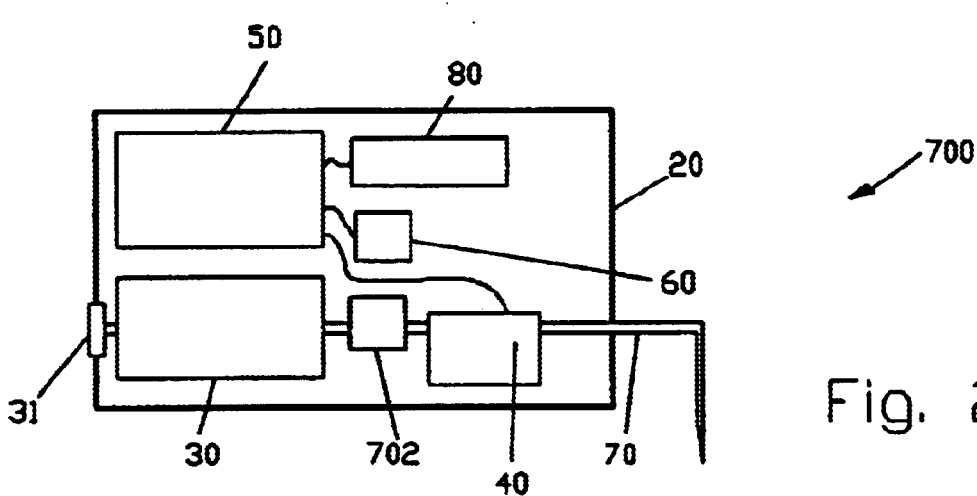
FIG. 27 is a schematic illustration of a further embodiment of a fluid delivery device constructed in accordance with the present disclosure.
Figure 28:
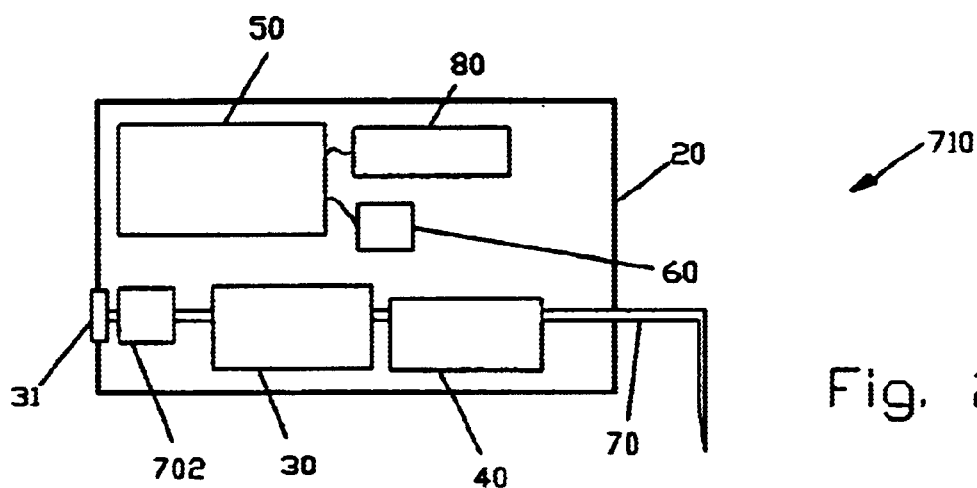
FIG. 28 is a schematic illustration of a further embodiment of a fluid delivery device constructed in accordance with the present disclosure.

Referring now to FIGS. 27 and 28, the invention also provides embodiments 700, 710 of the fluid delivery device including gas removal filters 702 for removing gas (e.g., air) bubbles from fluid injected into the devices from a patient. In general the gas removal filters 702 are constructed of material that allows the passage of gas therethrough, yet prevents fluid from passing therethrough. Gas removal filters are available, for example, from Pall Corporation of East Hills, N.Y. (www.pall.com). In the embodiment 700 of FIG. 27, the gas removal filter 702 is positioned between the reservoir 30 and the dispenser 40. In the embodiment 720 of FIG. 28, however, the gas removal filter 702 is positioned between a fill port 31 and the reservoir 30. Other embodiments are possible. For example, the device can be provided with a reservoir made from gas removal material instead of having a separate gas removal filter.

Due to issues of infection and contamination, it may be desirable to limit the fluid delivery device of the present invention to a single use. Referring to FIGS. 29a through 29d, the present invention, therefore, also provides a "single-use" fill port 800 for allowing the reservoir 30 of the fluid device to be filled only once. The fill port 800 includes a passageway 802 in fluid communication with the reservoir 30, a valve 804 positioned within the passageway and allowing one-way flow into the reservoir 30, and a removable needle insertion septum 806 sealing the passageway 802. The needle insertion septum 806 may be constructed of a resealing elastomer such as silicone that allows a needle 150 to puncture the septum 806 to add fluid to the reservoir 30, yet provides a seal around the needle 150.

Figure 29A:
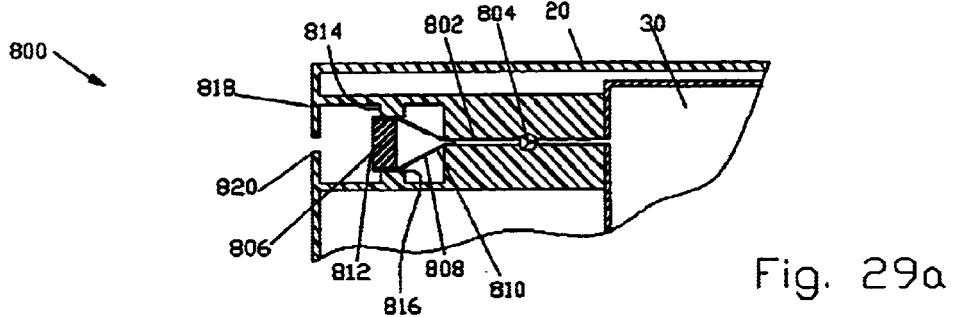
FIGS. 29a through 29d are sectional views of an embodiment of a fill port constructed in accordance with the present disclosure, and illustrating operation of the fill port.
Figure 29B:
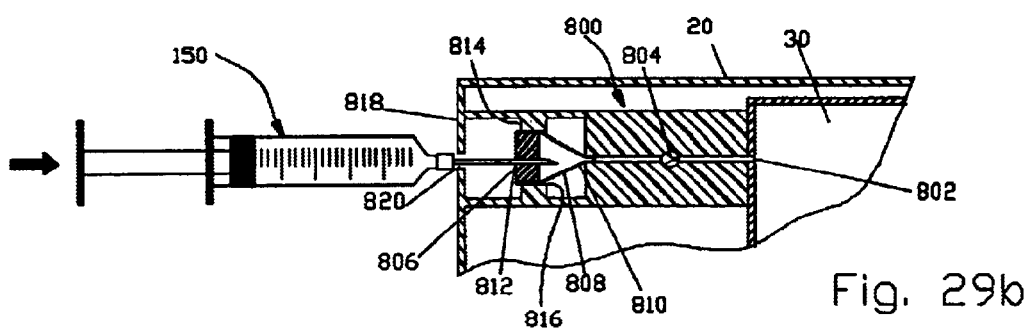
Figure 29C:
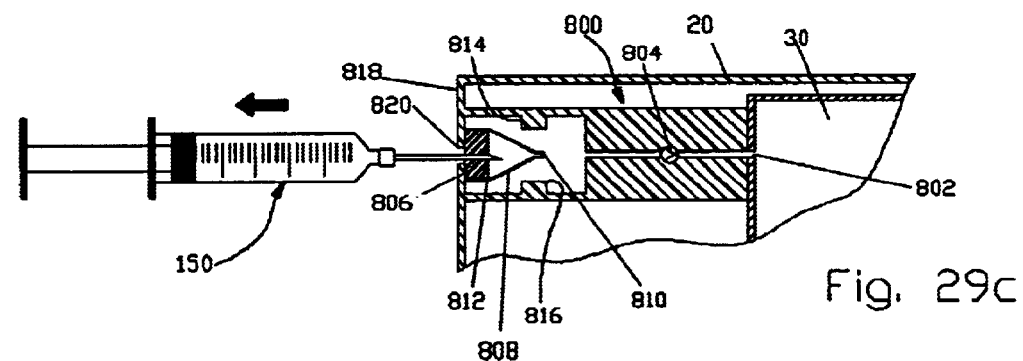
Figure 29D:
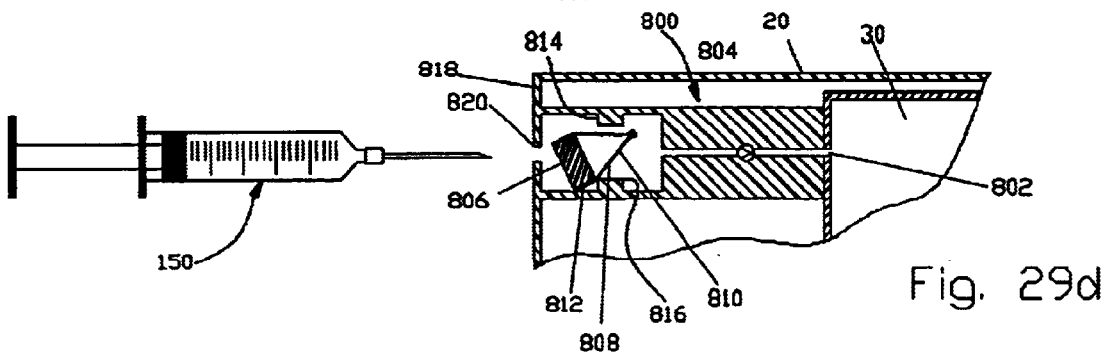

In the embodiment of FIGS. 29a through 29b, the fill port 800 includes a funnel 808 having a small open end 810 removably received in the passageway 802 and a large open end 812 receiving the septum 806. The fill port 800 also includes a first wall 814 having an opening 816 removably receiving the large open end 812 of the funnel when the small open end 810 of the funnel 808 is removably received in the passageway 802, as shown in FIGS. 29a and 29b. A second wall 818 is spaced from the first wall 814 more than a thickness of the septum 806 and has an opening 820 sized to allow passage of a needle 150, but prevent passage of the septum 806, as shown in FIGS. 29c and 29d. As shown in FIGS. 29c and 29d, removal of the needle 150 from the fill port 800 pulls the funnel 808 out of the passageway 802, and thus prevents further refills of the reservoir 30 through the fill port 800.

FIGS. 30a and 30b show another fill port 850 constructed in accordance with the present invention. The fill port 850 includes a first wall 852 having an opening 854 preventing passage of the septum 806, as shown in FIG. 30a, and a second wall 856 spaced from the first wall 852 at least about a thickness of the septum and having an opening 858 allowing passage of a needle 150. The second wall 856 and the opening of the second wall 858 are adapted to allow passage of the septum 806 upon at least a predetermined force applied to the septum. Preferably, the predetermined force is less than a force required to pull a needle 150 out of the septum 806, such that a withdrawn needle 150 pulls the septum 806 out of the fill port 850, as shown in FIG. 30b.

Referring to FIG. 31, the present invention also provides a fluid delivery device 900 having multiple subcutaneous access tools 970. Each access tool 970 is independently connected to the dispenser 40 through a passageway 972, and is initially retracted such that the passageway 972 is occluded. Each access tool 970 is also independently deployable. Upon deployment of each access tool 970, the passageway 972 of the deployed tool is released to allow fluid flow through the deployed tool. Preferably each access tool includes a rigid needle 974, as shown in FIG. 32.

The multiple, independently deployable needles 974 beneficially extend the useful life of the fluid delivery device 900. According to standards set by the Center for Disease Control (CDC), a single needle, such as an infusion needle or intravenous needle, should not remain deployed in a patient for more than three days, to minimize the chances for infection at the injection site through the skin of the patient. The present invention, therefore, increases the useable life of a single fluid delivery device 900 by providing the device with multiple, independently deployable needles 974. If the device is provided with three retractable needles 974, and each needle is used for the maximum allowable period of three days in accordance to CDC standards, for example, the life of the device 900 can be extended to nine days. The embodiment 900 of FIG. 31 is provided with three needles 974, but can be provided with two needles or more than three needles, as desired and appropriate.

Referring to the specific embodiment 900 as shown in FIG. 32, each needle 974 is manually deployable and includes a slidable lever 976 secured to the needle and extending out of the housing 20 of the device for patient access. The needle 974 is shown retracted in FIG. 32, with the passageway 972 occluded by an occlusion member 978 extending from the lever 976 and pinching the passageway 972 against a boss 980 extending from the housing wall 20. When the device 900 is attached to a skin surface of a patient, the patient simply slides the lever 976 towards the skin to release the passageway 972 and inject the needle 974 into the skin. After three days, the patient slides the lever 976 away from the skin to withdraw the needle 974 from the skin and occlude the passageway 972. The next needle can then be deployed. The device can also be provided with means for maintaining each of the needles 974 in an independent sterile condition prior to deployment, such as separate sealed membranes covering the needle opening in the housing 20 and that the needles puncture through during deployment.

Although exemplary embodiments of the invention have been shown and described, many changes, modifications and substitutions may be made by those having ordinary skill in the art without necessarily departing from the spirit and scope of this invention.

What is claimed is:

1. A device for delivering fluid to a patient, comprising:
 A) an exit port assembly adapted to connect to a transcutaneous patient access and
 B) a dispenser including,
  a first layer defining a passageway connected to the exit port assembly and an opening in fluid communication with the passageway,
  a resilient diaphragm received on the first layer covering the opening such that the opening and the diaphragm define an expandable accumulator,
  a second layer received over the diaphragm on the first layer, the second layer having a pulse chamber over the diaphragm and in alignment with the opening of the first layer, and a port in fluid communication with the pulse chamber, and
  a third layer received on the second layer and defining a secondary chamber in fluid communication with the port of the second layer,
 wherein the surface of the first layer further defines an occlusion sensor recess in the passageway.

2. A device according to claim 1, wherein the surface of the first layer further defines a valve seat in the passageway.

3. A device according to claim 1, further comprising a reservoir, and the dispenser controls fluid flow from the reservoir to the exit port assembly.

4. A device according to claim 3, wherein the reservoir contains a therapeutic fluid.

5. A device according to claim 3, further comprising a fill port connected to the reservoir.

6. A device according to claim 3, wherein the reservoir is pressurized.

7. A device according to claim 1, further comprising a transcutaneous patient access tool connected to the exit port assembly.

8. A device according to claim 1, further comprising a gas permeable reservoir for containing fluid, and the dispenser control fluid flow from the reservoir to the exit port assembly.

9. A device for delivering fluid to a patient, comprising:
A) an exit port assembly adapted to connect to a transcutaneous patient access and
B) a dispenser including,
a first layer defining a passageway connected to the exit port assembly and an opening in fluid communication with the passageway,
a resilient diaphragm received on the first layer covering the opening such that the opening and the diaphragm define an expandable accumulator,
a second layer received over the diaphragm on the first layer, the second layer having a pulse chamber over the diaphragm and in alignment with the opening of the first layer, and a port in fluid communication with the pulse chamber, and
a third layer received on the second layer and defining a secondary chamber in fluid communication with the port of the second layer,
wherein the first layer further defines a reservoir and a second passageway extending between the reservoir and the accumulator.

10. A device according to claim 9, further comprising an inlet valve controlling flow from the reservoir into the accumulator, and an outlet valve controlling flow between the accumulator and the exit port assembly.

11. A device for delivering fluid to a patient, comprising:
A) an exit port assembly adapted to connect to a transcutaneous patient access and
B) a dispenser including,
a first layer defining a passageway connected to the exit port assembly and an opening in fluid communication with the passageway,
a resilient diaphragm received on the first layer covering the opening such that the opening and the diaphragm define an expandable accumulator,
a second layer received over the diaphragm on the first layer, the second layer having a pulse chamber over the diaphragm and in alignment with the opening of the first layer, and a port in fluid communication with the pulse chamber, and
a third layer received on the second layer and defining a secondary chamber in fluid communication with the port of the second layer,
wherein the first layer further defines a reservoir and a second passageway extending between the reservoir and the accumulator, and a bubble removal bay and a third passageway extending between the bubble removal bay and the reservoir.

12. A device for delivering fluid to a patient, comprising:
an exit port assembly adapted to connect to a transcutaneous patient access tool:
a dispenser including at least two laminated layers of material defining a passageway connected to the exit port assembly, and an expandable accumulator in fluid communication with the passageway;
a local processor connected to the dispenser and programmed to cause the dispenser to allow fluid flow from a reservoir to the exit port assembly based on flow instructions;
a wireless receiver connected to the local processor for receiving flow instructions from a separate, remote control device and delivering the flow instructions to the local processor; and
a housing containing the exit port assembly, the dispenser, the local processor, and the wireless receiver, wherein the housing is free of user input components for providing flow instructions to the local processor.

13. A system comprising:
a device for delivering fluid to a patient, including:
an exit port assembly adapted to connect to a transcutaneous patient access tool;
a dispenser including at least two laminated layers of material defining a passageway connected to the exit port assembly, and an expandable accumulator in fluid communication with the passageway;
a local processor connected to the dispenser and programmed to cause the dispenser to allow fluid flow from a reservoir to the exit port assembly based on flow instructions;
a wireless receiver connected to the local processor for receiving flow instructions from a separate, remote control device and delivering the flow instructions to the local processor; and
a housing containing the exit port assembly, the dispenser, the local processor and the wireless receiver, wherein the housing is free of user input components for providing flow instructions to the local processor; and
a remote control device separate from the fluid delivery device and including:
a remote processor;
user interface components connected to the remote processor for allowing a user to provide flow instructions to the remote processor; and
a transmitter connected to the remote processor for transmitting the flow instructions to the receiver of the fluid delivery device.

14. A device for delivering fluid to a patient comprising:
an exit port assembly adapted to connect to a transcutaneous patient access tool;
a dispenser including at least two laminated layers of material defining a passageway connected to the exit port assembly, and an expandable accumulator in fluid communication with the passageway;
a local processor connected to the dispenser and programmed to cause the dispenser to allow fluid flow from a reservoir to the exit port assembly based on flow instructions, and further programmed to provide flow information;
a wireless transmitter connected to the local processor for transmitting the flow information from the local processor to a separate, remote control device; and
a housing containing the exit port assembly, the dispenser, the local processor, and the wireless transmitter, wherein the housing is free of user output components for providing the flow information from the local processor to a user.

15. A system comprising:
a device for delivering fluid to a patient, including:
- an exit port assembly adapted to connect to a transcutaneous patient access tool;
- a dispenser including at least two laminated layers of material defining a passageway connected to the exit port assembly, and an expandable accumulator in fluid communication with the passageway;
- a local processor connected to the dispenser and programmed to cause the dispenser to allow fluid flow from a reservoir to the exit port assembly based on flow instructions, and further programmed to provide flow information;
- a wireless transmitter connected to the local processor for transmitting the flow information from the local processor to a separate, remote control device; and
- a housing containing the exit port assembly, the dispenser, the local processor, and the wireless transmitter, wherein the housing is free of user output components for providing the flow information from the local processor to a user; and a remote control device separate from the fluid delivery device and including:
- a remote processor;
- user output components connected to the remote processor for allowing a user to receive flow information; and
- a receiver connected to the remote processor for receiving the flow information from the transmitter of the fluid delivery device.

16. A device for delivering fluid to a patient comprising:

an exit port assembly adapted to connect to a transcutaneous patient access tool;

a dispenser including at least two laminated layers of material defining a passageway connected to the exit port assembly, and an expandable accumulator in fluid communication with the passageway;

a reservoir, and the dispenser controls fluid flow from the reservoir to the exit port assembly;

a fill port; and a gas removal filter connecting the fill port to the reservoir.

* * * * *

UNITED STATES PATENT AND TRADEMARK OFFICE
CERTIFICATE OF CORRECTION

PATENT NO.    : 6,669,669 B2
DATED         : December 30, 2003
INVENTOR(S)   : J. Christopher Flaherty et al.

It is certified that error appears in the above-identified patent and that said Letters Patent is hereby corrected as shown below:

<u>Column 20,</u>
Line 47, after "access", insert -- tool --;

<u>Column 21,</u>
Lines 19 and 44, after "access", insert -- tool --.

Signed and Sealed this

Twenty-seventh Day of April, 2004

JON W. DUDAS
*Acting Director of the United States Patent and Trademark Office*